(12) United States Patent
Perrett et al.

(10) Patent No.: US 12,290,598 B2
(45) Date of Patent: *May 6, 2025

(54) ORALLY ADMINISTERED CORTICOSTEROID COMPOSITIONS

(71) Applicant: Ellodi Pharmaceuticals, L.P., Lawrenceville, NJ (US)

(72) Inventors: Stephen Perrett, Princeton, NJ (US); Fredric Jay Cohen, Washington Crossing, PA (US); Gopi M. Venkatesh, Vandalia, OH (US)

(73) Assignee: Ellodi Pharmaceuticals, L.P., Lawrenceville, NJ (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/569,047

(22) Filed: Jan. 5, 2022

(65) Prior Publication Data

US 2022/0339098 A1  Oct. 27, 2022

Related U.S. Application Data

(60) Continuation of application No. 16/821,464, filed on Mar. 17, 2020, now Pat. No. 11,246,828, which is a continuation of application No. 15/816,154, filed on Nov. 17, 2017, now Pat. No. 10,632,069, which is a continuation of application No. 15/205,390, filed on Jul. 8, 2016, now Pat. No. 9,849,084, which is a continuation of application No. 14/311,732, filed on Jun. 23, 2014, now Pat. No. 9,387,167, which is a division of application No. 12/896,005, filed on Oct. 1, 2010, now Pat. No. 8,771,729.

(60) Provisional application No. 61/247,642, filed on Oct. 1, 2009.

(51) Int. Cl.
| | |
|---|---|
| *A61K 9/00* | (2006.01) |
| *A61K 9/06* | (2006.01) |
| *A61K 9/08* | (2006.01) |
| *A61K 31/56* | (2006.01) |
| *A61K 31/569* | (2006.01) |
| *A61K 31/58* | (2006.01) |
| *A61K 45/06* | (2006.01) |
| *A61K 47/38* | (2006.01) |

(52) U.S. Cl.
CPC .......... *A61K 9/0065* (2013.01); *A61K 9/0053* (2013.01); *A61K 9/0056* (2013.01); *A61K 9/006* (2013.01); *A61K 9/08* (2013.01); *A61K 31/56* (2013.01); *A61K 31/569* (2013.01); *A61K 31/58* (2013.01); *A61K 45/06* (2013.01); *A61K 47/38* (2013.01); *A61K 9/06* (2013.01)

(58) Field of Classification Search
None
See application file for complete search history.

(56) References Cited

U.S. PATENT DOCUMENTS

| | | |
|---|---|---|
| 3,705,172 A | 12/1972 | Buchel et al. |
| 3,929,768 A | 12/1975 | Brattsand et al. |
| 4,080,448 A | 3/1978 | Mirsky |
| 4,335,121 A | 6/1982 | Phillipps et al. |
| 4,363,806 A | 12/1982 | Bergstrom et al. |
| 4,472,393 A | 9/1984 | Shapiro |
| 4,985,418 A | 1/1991 | Richards |
| 5,135,740 A | 8/1992 | Katz et al. |
| 5,252,337 A | 10/1993 | Powell |
| 5,278,175 A | 1/1994 | Ray et al. |
| 5,403,893 A | 4/1995 | Tanaka et al. |
| 5,446,070 A | 8/1995 | Mantelle |
| 5,482,934 A | 1/1996 | Calatayud et al. |
| 5,639,475 A | 6/1997 | Bettman et al. |
| 5,776,433 A | 7/1998 | Tzou et al. |
| 5,863,910 A | 1/1999 | Bolonick et al. |
| 6,139,865 A | 10/2000 | Friend et al. |
| 6,171,617 B1 | 1/2001 | Gruber |
| 6,316,027 B1 | 11/2001 | Johnson et al. |
| 6,495,160 B2 | 12/2002 | Esposito et al. |
| 6,534,549 B1 | 3/2003 | Newton et al. |
| 6,596,298 B2 | 7/2003 | Leung et al. |
| 6,596,311 B1 | 7/2003 | Dobetti |
| 6,740,332 B2 | 5/2004 | Zyck et al. |
| 7,033,606 B1 | 4/2006 | Besse et al. |
| 7,122,198 B1 | 10/2006 | Singh et al. |
| 7,125,564 B2 | 10/2006 | Chen et al. |
| 7,229,641 B2 | 6/2007 | Cherukuri |
| 8,077,288 B2 | 12/2011 | Kawashima |
| 8,545,881 B2 | 10/2013 | Venkatesh et al. |
| 8,580,300 B2 | 11/2013 | Wilhelm et al. |
| 8,679,545 B2 | 3/2014 | Dohil et al. |

(Continued)

FOREIGN PATENT DOCUMENTS

| | | |
|---|---|---|
| CA | 1027864 A | 3/1978 |
| CA | 2430481 A1 | 6/2002 |

(Continued)

OTHER PUBLICATIONS

U.S. Appl. No. 12/896,005, filed Oct. 1, 2010, US 2011-0081411 A1, Apr. 7, 2011, U.S. Pat. No. 8,771,729, Jul. 8, 2014.

(Continued)

*Primary Examiner* — Aradhana Sasan
(74) *Attorney, Agent, or Firm* — COOLEY LLP

(57) ABSTRACT

The present invention is directed to orally administered corticosteroid compositions. The present invention also provides a method for treating a condition associated with inflammation of the gastrointestinal tract in an individual. The method comprises administering to an individual in need thereof a pharmaceutical composition of the present invention.

34 Claims, No Drawings

(56) References Cited

U.S. PATENT DOCUMENTS

| | | |
|---|---|---|
| 8,771,729 B2 | 7/2014 | Perrett et al. |
| 8,932,596 B2 | 1/2015 | Benhamou et al. |
| 9,387,167 B2 | 7/2016 | Perrett et al. |
| 9,486,407 B2 | 11/2016 | Perrett et al. |
| 9,782,347 B2 | 10/2017 | Dohil et al. |
| 9,849,084 B2 | 12/2017 | Perrett et al. |
| 9,867,780 B2 | 1/2018 | Greinwald et al. |
| 10,076,494 B2 | 9/2018 | Pevzner et al. |
| 10,105,315 B2 | 10/2018 | Meltzer et al. |
| 10,176,301 B2 | 1/2019 | Hill et al. |
| 10,272,037 B2 | 4/2019 | Dohil et al. |
| 10,471,071 B2 | 11/2019 | Gosselin et al. |
| 10,632,069 B2 | 4/2020 | Perrett et al. |
| 10,869,592 B2 | 12/2020 | Ouyang et al. |
| 11,026,887 B2 | 6/2021 | Meltzer et al. |
| 11,166,961 B2 | 11/2021 | Gosselin et al. |
| 11,246,828 B2 | 2/2022 | Perrett et al. |
| 11,260,061 B2 | 3/2022 | Gosselin et al. |
| 11,266,598 B2 | 3/2022 | Perrett et al. |
| 11,684,571 B2 | 6/2023 | Meltzer et al. |
| 11,896,710 B2 | 2/2024 | Meltzer et al. |
| 12,059,494 B2 | 8/2024 | Meltzer et al. |
| 2001/0006625 A1 | 7/2001 | Bohn et al. |
| 2001/0014340 A1 | 8/2001 | Ohta et al. |
| 2003/0050312 A1 | 3/2003 | Hjorth et al. |
| 2003/0054036 A1 | 3/2003 | Liggins et al. |
| 2003/0099701 A1 | 5/2003 | Takaishi et al. |
| 2003/0215500 A1 | 11/2003 | Ohta et al. |
| 2004/0009212 A1 | 1/2004 | Tsai |
| 2004/0053902 A1 | 3/2004 | Smith |
| 2004/0106663 A1 | 6/2004 | Talley et al. |
| 2004/0228919 A1 | 11/2004 | Houghton et al. |
| 2004/0265375 A1 | 12/2004 | Platteeuw et al. |
| 2005/0009848 A1 | 1/2005 | Brantl |
| 2005/0112188 A1 | 5/2005 | Eliaz et al. |
| 2005/0232988 A1 | 10/2005 | Venkatesh et al. |
| 2006/0051414 A1 | 3/2006 | Ramalho et al. |
| 2006/0105038 A1 | 5/2006 | Lai et al. |
| 2006/0134054 A1 | 6/2006 | Kulkarni et al. |
| 2006/0292099 A1 | 12/2006 | Milburn et al. |
| 2007/0020330 A1 | 1/2007 | Dang et al. |
| 2007/0059361 A1 | 3/2007 | Rawas-Qalaji et al. |
| 2007/0111978 A1 | 5/2007 | Dohil et al. |
| 2009/0074862 A1 | 3/2009 | Schioppi et al. |
| 2009/0123390 A1 | 5/2009 | Hill |
| 2009/0123550 A1 | 5/2009 | Phillips et al. |
| 2009/0123551 A1 | 5/2009 | Phillips et al. |
| 2009/0131386 A1 | 5/2009 | Phillips |
| 2009/0149433 A1 | 6/2009 | Phillips |
| 2009/0155360 A1 | 6/2009 | Venkatesh et al. |
| 2009/0169620 A1 | 7/2009 | Venkatesh et al. |
| 2009/0181099 A1 | 7/2009 | Dohil et al. |
| 2009/0191275 A1 | 7/2009 | Dohil et al. |
| 2009/0264392 A1 | 10/2009 | Warndahl et al. |
| 2010/0034894 A1 | 2/2010 | Szymczak et al. |
| 2010/0215753 A1 | 8/2010 | Sherwood et al. |
| 2010/0216754 A1 | 8/2010 | Hill |
| 2011/0081411 A1 | 4/2011 | Perrett et al. |
| 2011/0097401 A1 | 4/2011 | Phillips et al. |
| 2011/0123460 A1 | 5/2011 | Wilhelm et al. |
| 2011/0129530 A1 | 6/2011 | Venkatesh et al. |
| 2012/0128764 A1 | 5/2012 | Venkatesh et al. |
| 2012/0164080 A1 | 6/2012 | Hill et al. |
| 2012/0282335 A1 | 11/2012 | Venkatesh et al. |
| 2013/0296286 A1 | 11/2013 | Dohil et al. |
| 2013/0310661 A1 | 11/2013 | Jedwab et al. |
| 2014/0187523 A1 | 7/2014 | Dohil et al. |
| 2014/0228714 A1 | 8/2014 | Chau et al. |
| 2014/0287051 A1 | 9/2014 | Perrett et al. |
| 2014/0303131 A1 | 10/2014 | Perrett et al. |
| 2015/0209432 A1 | 7/2015 | Konda et al. |
| 2015/0231156 A1 | 8/2015 | Phillips et al. |
| 2016/0045518 A1 | 2/2016 | Dohil et al. |
| 2016/0078186 A1 | 3/2016 | Hill et al. |
| 2016/0206627 A1 | 7/2016 | Gosselin et al. |
| 2016/0213681 A1 | 7/2016 | Santus et al. |
| 2016/0324772 A1 | 11/2016 | Greinwald et al. |
| 2017/0071855 A1 | 3/2017 | Perrett et al. |
| 2017/0183719 A1 | 6/2017 | Rothenberg et al. |
| 2018/0071211 A1 | 3/2018 | Dohil et al. |
| 2018/0133145 A1 | 5/2018 | Meltzer et al. |
| 2018/0153802 A1 | 6/2018 | Perrett et al. |
| 2019/0008760 A1 | 1/2019 | Meltzer et al. |
| 2019/0201333 A1 | 7/2019 | Dohil et al. |
| 2020/0016171 A1 | 1/2020 | Gosselin et al. |
| 2020/0214979 A1 | 7/2020 | Perrett et al. |
| 2020/0368147 A1 | 11/2020 | Meltzer et al. |
| 2020/0381097 A1 | 12/2020 | Meltzer |
| 2021/0205328 A1 | 7/2021 | Gosselin et al. |
| 2021/0244660 A1 | 8/2021 | Perrett et al. |
| 2021/0275438 A1 | 9/2021 | Meltzer et al. |
| 2021/0346278 A1 | 11/2021 | Meltzer et al. |
| 2022/0110945 A1 | 4/2022 | Gosselin et al. |
| 2022/0347189 A1 | 11/2022 | Nezamis et al. |
| 2023/0414498 A1 | 12/2023 | Meltzer et al. |
| 2024/0207288 A1 | 6/2024 | Eagle |

FOREIGN PATENT DOCUMENTS

| | | |
|---|---|---|
| CA | 2704946 A1 | 5/2009 |
| CA | 2776164 A1 | 4/2011 |
| CL | 38272008 | 12/2007 |
| CN | 1186428 A | 7/1998 |
| CN | 102665722 A | 9/2012 |
| CN | 105392497 A | 3/2016 |
| DE | 2323215 A1 | 11/1973 |
| DE | 4129535 A1 | 3/1992 |
| DE | 60202794 T2 | 5/2006 |
| DE | 202010018594 U1 | 2/2018 |
| EP | 0057401 A1 | 8/1982 |
| EP | 0440372 A1 | 8/1991 |
| EP | 1310243 A1 | 5/2003 |
| EP | 1323417 A1 | 7/2003 |
| EP | 1595533 A1 | 11/2005 |
| EP | 2886108 A1 | 6/2015 |
| EP | 2211896 B1 | 1/2018 |
| EP | 2482822 B1 | 8/2018 |
| EP | 2214679 B1 | 3/2019 |
| EP | 3041476 B1 | 11/2019 |
| EP | 3354276 B1 | 1/2020 |
| JP | S56138200 A | 10/1981 |
| JP | 11130679 A | 5/1999 |
| JP | H11511162 A | 9/1999 |
| JP | 2001524094 A | 11/2001 |
| JP | 2002521321 A | 7/2002 |
| JP | 2003509359 A | 3/2003 |
| JP | 2003261439 A | 9/2003 |
| JP | 2003292459 A | 10/2003 |
| JP | 2006077018 A | 3/2006 |
| JP | 2006516616 A | 7/2006 |
| JP | 2006516646 A | 7/2006 |
| JP | 2006524650 A | 11/2006 |
| JP | 2009519793 A | 5/2009 |
| JP | 2009521523 A | 6/2009 |
| JP | 2009173552 A | 8/2009 |
| JP | 2011503073 A | 1/2011 |
| JP | 2013506683 A | 2/2013 |
| KR | 20060123160 A | 12/2006 |
| KR | 20100087007 A | 8/2010 |
| KR | 20120104975 A | 9/2012 |
| KR | 20160058829 A | 5/2016 |
| RU | 2011134040 A | 2/2013 |
| RU | 2016104400 A | 8/2017 |
| WO | WO-9632095 A1 | 10/1996 |
| WO | WO-9706786 A1 | 2/1997 |
| WO | WO-9847535 A1 | 10/1998 |
| WO | WO-9947144 A1 | 9/1999 |
| WO | WO-0044351 A1 | 8/2000 |
| WO | WO-0064450 A1 | 11/2000 |
| WO | WO-0119342 A2 | 3/2001 |
| WO | WO-02092057 A1 | 11/2002 |
| WO | WO-03039520 A1 | 5/2003 |
| WO | WO-03093344 A1 | 11/2003 |
| WO | WO-2004064810 A1 | 8/2004 |

(56) References Cited

FOREIGN PATENT DOCUMENTS

| WO | WO-2004067004 A1 | 8/2004 |
| WO | WO-2004069225 A1 | 8/2004 |
| WO | WO-2004091585 A1 | 10/2004 |
| WO | WO-2005087194 A1 | 9/2005 |
| WO | WO-2007071179 A1 | 6/2007 |
| WO | WO-2007074472 A2 | 7/2007 |
| WO | WO-2008098634 A1 | 8/2008 |
| WO | WO-2009064457 A2 | 5/2009 |
| WO | WO-2009064458 A2 | 5/2009 |
| WO | WO-2009064819 A2 | 5/2009 |
| WO | WO-2009086046 A1 | 7/2009 |
| WO | WO-2009098595 A2 | 8/2009 |
| WO | WO-2010021636 A1 | 2/2010 |
| WO | WO-2010144865 A2 | 12/2010 |
| WO | WO-2011041509 A1 | 4/2011 |
| WO | WO-2015006571 A1 | 1/2015 |
| WO | WO-2015034678 A2 | 3/2015 |
| WO | WO-2015035114 A1 | 3/2015 |
| WO | WO-2017189805 A1 | 11/2017 |
| WO | WO-2018035393 A1 | 2/2018 |
| WO | WO-2019165138 A1 | 8/2019 |
| WO | WO-2021067585 A1 | 4/2021 |
| WO | WO-2022020464 A1 | 1/2022 |
| WO | WO-2022225892 A1 | 10/2022 |
| ZA | 6805392 | 6/1969 |

OTHER PUBLICATIONS

U.S. Appl. No. 14/294,660, filed Jun. 3, 2014, US 2014-0287051 A1, Sep. 25, 2014, U.S. Pat. No. 9,486,407, Nov. 8, 2016.

U.S. Appl. No. 14/311,732, filed Jun. 23, 2014, US 2014-0303131 A1, Oct. 9, 2014, U.S. Pat. No. 9,387,167, Jul. 12, 2016.

U.S. Appl. No. 15/205,390, filed Jul. 8, 2016, US 2017-0071855 A1, Mar. 16, 2017, U.S. Pat. No. 9,849,084, Dec. 26, 2017.

U.S. Appl. No. 15/816,154, filed Nov. 17, 2017, US 2018-0153802 A1, Jun. 7, 2018, U.S. Pat. No. 10,632,069, Apr. 28, 2020.

U.S. Appl. No. 16/821,464, filed Mar. 17, 2020, US 2020-0214979 A1, Jul. 9, 2020, U.S. Pat. No. 11,246,828, Feb. 15, 2022.

U.S. Appl. No. 17/236,295, filed Apr. 21, 2021, US 2021-0244660 A1, Aug. 12, 2021, U.S. Pat. No. 11,266,598, Mar. 8, 2022.

Sodikoff et al., "Therapeutic strategies in eosinophilic esophagitis: Induction, maintenance and refractory disease", Best Pract Res Clin Gastroenterol. (Oct. 2015); 29(5): 829-839.

Straumann et al., "Budesonide is effective in adolescent and adult patients with active eosinophilic esophagitis", Gastroenterology (Nov. 2010); 139(5): 1526-1537.

Straumann et al., "Long-term budesonide maintenance treatment is partially effective for patients with eosinophilic esophagitis", Clin Gastroenterol Hepatol. (May 2011); 9(5): 400-409.

Gentile et al., "Oesophageal narrowing is common and frequently under-appreciated at endoscopy in patients with oesophageal eosinophilia". Alimentary Pharmacology & Therapeutics (Dec. 2014); 40(11-12): 1333-1340. Epub Oct. 7, 2014.

German Patent Complaint Proceedings in the Regional Court, Mannheim, *Ellodi Pharmaceuticals, L.P.* vs. *Dr. Falk Pharma GmbH*, Docket No. 7 O 75/19, communication from the Regional Court of Mannheim giving Dr. Falk Pharma GmbH the opportunity to comment on the withdrawal of the complaint, dated Jul. 12, 2022, and Machine English translation, 2 pages.

German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Notice of termination of proceedings dated Aug. 16, 2022, and English translation, 2 pages.

German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Withdrawal of cancellation action dated Jul. 20, 2022, 1 page.

Opposition Proceedings in European Patent No. EP 2482822, Appeal No. T1954/21-3.3.01 (Appln. No. 10821232.5), filed by Dr. Falk Pharma GmbH on Mar. 1, 2019; EPO Communication dated Jul. 25, 2022 regarding Termination of opposition proceedings, 1 page.

Opposition Proceedings in European Patent No. EP 3086782 (Appln. No. 14814872.9), (in the name of Dr. Falk Pharma GmbH) filed by Ellodi Pharmaceuticals, L.P. on Jun. 26, 2019; Written decision on rejection of the opposition dated May 9, 2022, and English translation, 63 pages.

Opposition Proceedings in European Patent No. EP 3403654 (Appln. No. 18178891.0), filed by Dr. Falk Pharma GmbH; Decision to discontinue the opposition proceedings dated Sep. 5, 2022, 2 pages.

PCT/US2022/025297, International Search Report and Written Opinion mailed Jul. 29, 2022, 10 pages.

Takita et al., "Successful esophageal endoscopic submucosal dissection with a transoral endoscope after stepwise scope bougienage of post-endoscopic submucosal dissection stricture". JGH Open (Oct. 22, 2020); 5(1): 163-165. eCollection Jan. 2021.

Dellon E.S., "Safety and Efficacy of Budesonide Oral Suspension Maintenance Therapy in Patients With Eosinophilic Esophagitis", Clin Gastroenterol Hepatol. Mar. 2019; 17(4): 666-673.e8. Epub Jun. 12, 2018.

Extended European Search Report for European Application No. EP 20873169.5 dated Sep. 22, 2023, 9 pages.

Hirano, I., et al. "Randomised clinical trial: the safety and tolerability of fluticasone propionate orally disintegrating tablets versus placebo for eosinophilic oesophagitis", Aliment Pharmacol Ther. Apr. 2020;51(8):750-759. Epub Mar. 9, 2020.

Konikoff, et al., "A Randomized, Double-Blind, Placebo-Controlled Trial of Fluticasone Propionate for Pediatric Eosinophilic Esophagitis". Gastroenterology. Nov. 2006; 131(5): 1381-1391. Epub Aug. 16, 2006.

Schoepfer, et al., "Delay in diagnosis of eosinophilic esophagitis increases risk for stricture formation in a time-dependent manner". Gastroenterology. Dec. 2013; 145(6): 1230-1236. Epub Aug. 13, 2013.

Straumann et al., "Budesonide Orodispersible Tablets Maintain Remission in a Randomized, Placebo-Controlled Trial of Patients With Eosinophilic Esophagitis". Gastroenterology. Nov. 2020; 159(5): 1672-1685. e5. Epub Jul. 25, 2020.

Aceves, et al., "Oral viscous budesonide: a potential new therapy for eosinophilic esophagitis in children". Am J Gastroenterol. (Oct. 2007); 102(10): 1-9. Epub Jun. 20, 2007.

Aceves, et al., "Topical viscous budesonide suspension for treatment of eosinophilic esophagitis". The Journal of Allergy and Clinical Immunology (Sep. 1, 2005); vol. 116, Issue 3, pp. 705-706. Epub Jul. 1, 2005.

Ahmed and Shah, "Formulation of low dose medicines—theory and practice." Am. Pharm. Rev (2000); 3(3): 9-14.

Ahmed, Monjur, "Eosinophilic esophagitis in adults: An update". World J Gastrointest Pharmacol Ther. (May 6, 2016); 7(2): 207-213.

Alexander, et al., "Review. Therapeutic Options for Eosinophilic Esophagitis". Gastroenterology & Hepatology (Jan. 1, 2011); 7(1): 59-61.

Auszug von European Pharmacopeia 6.0 (English language) 2.9.8; Jul. 23, 2007, 2 pages.

Auszug von European Pharmacopeia 8.0 (German language) 2.9.8; Jul. 15, 2013, 1 page.

Auszug von US Pharmacopeia 35 1217; May 1, 2012, 3 pages.

[Author Unknown] Definition of slow-release (downloaded from Merriam-Webster online athttps://www.merriam-webster.com/medical/slow-release); accessed Jul. 31, 2019, 1 page.

[Author Unknown] Definition of sustained-release (downloaded from Merriam-Webster online athttps://www.merriam-webster.com/dictionary/sustainedrelease#medicalDictionary); accessed Jul. 31, 2019, 1 page.

[Author unknown] DrugBank Accession Number, first approved 1990, DrugBank Accession No. DB00588, https://go.drugbank.com/drugs/DB00588, 14 pages.

[Author Unknown] Jorveza package leaflet (downloaded from the European Medicines Agency atwww.ema.europa.eu/en/medicines/human/EPAR/jorveza#product-informationsection); accessed Aug. 1, 2019, 8 pages.

(56) References Cited

OTHER PUBLICATIONS

[Author Unknown] Jorveza package leaflet, Jorveza 1mg orodispersible tablets, tablets package leaflet (PIL) for United Kingdom-Ireland, Mat-No. 1147370 (Losan Pharma), Dated Mar. 15, 2018, Date Code Falk: GB-IE/03.18, 2 pages.
[Author Unknown] Jorveza summary of product characteristics (downloaded from the European Medicines Agency atwww.ema.europa.eu/en/medicines/human/EPAR/jorveza#product-informationsection); first published Jan. 18, 2018, accessed Aug. 1, 2019, 9 pages.
[Author Unknown] Povidone (polyvinylpyrrolidone (PVP)) compound summary (downloaded from Wikipedia at https://en.wikipedia.org/wiki/Polyvinylpyrrolidone); accessed Jul. 31, 2019, 5 pages.
[Author Unknown] Solubility of budesonide (downloaded fromhttps://pubchem.ncbi.nlm.nih.gov/compound/Budesonide#section=Solubility&fullscreen=true); information available as of Oct. 15, 2015, accessed Aug. 1, 2019, 1 page.
Author Unknown, WHT 3ME brochure Version 2.0; Fully Automated 4 in 1 Tablet Testing Instrument Pharma Test; publication date unknown.
Bauer, et al., "106 Chapter 5 Methods and Basic Operations". Lehrbuch der Pharmazeutischen Technologie (Textbook of pharmaceutical technology), With an introduction to biopharmacy (2006); (eds) Lippold, et al., 8th revised and updated edition, and English translation, 12 pages.
Beveridge, et al., "Novel Therapeutic Approaches to Eosinophilic Esophagitis". Gastroenterology & Hematology (Jun. 2020); 16(6): 294-301.
Bonnet, et al., "Formulation of a 3-months Stability Oral Viscous Budesonide Gel and Development of an Indicating Stability HPLC Method", Pharm Technol Hosp Pharm (2018); 3(2): 91-99.
Bower et al., "Manifestations and Treatment of Laryngeal Sarcoidosis". Am. Rev. Respir. Dis., 122(2): 325-332 (1980).
Breuer, et al., "Glossary of Terms Related to Pharmaceutics (IUPAC Recommendations 2009)" Pure Appl. Chem. (2009); 81 (5): 971-999.
Brunner, et al., "Gastrointestinal transit, release and plasma pharmacokinetics of a new oral budesonide formulation." British Journal of Clinical Pharmacology (2005); 61(1): 31-38.
Buckton, G., "Water sorption and near IR spectroscopy to study the differences between microcrystalline cellulose and silicified microcrystalline cellulose before and after wet granulation." International Journal of Pharmaceutics (Apr. 1999); 181 (1): 41-47.
Budesonid, https://www.chemie.de/lexikon/Budesonid.html, Jul. 12, 2019, and English version, Sep. 10, 2020, 3 pages.
Campieria et al., "Oral budesonide is as effective as oral prednisolone in active Crohn's disease," Gut, 41: 209-214 (1997).
Certified copy of Priority Document U.S. Appl. No. 61/186,777, filed Jun. 12, 2009, 104 pages.
Daley-Yates, Peter T. "Inhaled corticosteroids: potency, dose equivalence and therapeutic index." British Journal of Clinical Pharmacology (2015); 80(3): 372-380.
Declaration of Stephen Perrett, MBA, Ph.D. dated Jul. 16, 2020, 6 pages.
Dellon, et al., "Efficacy of Budesonide vs Fluticasone for Initial Treatment of Eosinophilic Esophagitis in a Randomized Controlled Trial". Gastroenterology (2019); 157: 65-73.
Dilger, K., et al. "Active eosinophilic esophagitis is associated with impaired elimination of budesonide by cytochrome P450 3A enzymes." Digestion (2013); 87(2):110-117. Epub Jan. 25, 2013.
Dohil, et al., "Oral Viscous Budesonide is Effective in Children With Eosinophilic Esophagitis in a Randomized, Placebo-Controlled Trial". Gastroenterol. (Aug. 2010); 139(2): 418-429.
Dolo-Dobendan®, 1.4 mg/10 mg lozenges package insert, Reference ID 3030657, Revised: Jan. 2015, with English translation, 7 pages.
Dr. Schleuniqer, "Key factors influencing measured tablet hardness"; Pharmatron; 2011, 5 pages.
EPO Communication dated Apr. 25, 2019 in connection with Application No. EP 08848597.4, 13 pages.

Eurasian Application No. 201491358, Search Report (with English translation), issued Jan. 22, 2015, 4 pages.
European Application No. EP 19757814.9, Extended European Search Report dated Nov. 4, 2021, 11 pages.
European Application No. EP 10821232.5, Extended European Search Report dated Feb. 6, 2014, 10 pages.
European Application No. EP 14184844.0, Extended European Search Report dated Feb. 9, 2015, 7 pages.
European Application No. EP 14842811.3, Extended European Search Report dated Mar. 23, 2017, 6 pages.
European Application No. EP 17842162.4, Extended European Search Report dated Apr. 1, 2020, 8 pages.
European Application No. EP 18178891.0, Extended European Search Report dated Aug. 13, 2018, 3 pages.
European Application No. EP 19189185.2, Extended European Search Report dated Aug. 29, 2019, 9 pages.
European Application No. EP 19207287.4, Extended European Search Report dated Apr. 6, 2020, 9 pages.
Falcoz, et al., "Bioavailability of Orally Administered Micronised Fluticasone Propionate." Clinical Pharmacokinetics (2000); 39 Suppl. 1: 9-15.
Forum of the National Formulary of Japan, compilation, Drugs in Japan, 2009 edition, published 2008, p. 2161-2165 (and English translation/summary of pertinent paragraphs), 8 pages.
Furuta, et al., "Review article: the pathogenesis and management of eosinophilic oesophagitis". Alimentary Pharmacology & Therapeutics (2006); 24: 172-182.
Furuta, Glenn T., "Eosinophils in the Esophagus: Acid is Not the Only Cause". Journal of Pediatric Gastroenterology & Nutrition (Apr. 1998); 26(4): 468-471.
Furuta, Glenn T., et al. "Eosinophilic esophagitis in children and adults: a systematic review and consensus recommendations for diagnosis and treatment: sponsored by the American Gastroenterological Association (AGA) Institute and North American Society of Pediatric Gastroenterology, Hepatology, and Nutrition." Gastroenterology (2007); 133(4): 1342-1363.
Georgia Application No. AP 2010012674, Search Report (with English translation) dated Nov. 28, 2013, 11 pages.
German Patent Complaint Proceedings in the Regional Court, Mannheim, *Ellodi Pharmaceuticals, L.P. (formerly Adare Development I, L.P.) vs. Dr. Falk Pharma GmbH*, Docket No. 7 O 75/19, Defendant's Consent to Withdrawal filed Jul. 15, 2022, and English translation, 2 pages.
German Patent Complaint Proceedings in the Regional Court, Mannheim, *Ellodi Pharmaceuticals, L.P. vs. Dr. Falk Pharma GmbH*, Docket No. 7 O 75/19, Order concerning value under dispute dated Jul. 18, 2022, and English translation, 4 pages.
German Patent Complaint Proceedings in the Regional Court, Mannheim, *Ellodi Pharmaceuticals, L.P. vs. Dr. Falk Pharma GmbH*, Docket No. 7 O 75/19, Withdrawal Submission filed by Ellodi Pharmaceuticals, L.P., dated Jul. 11, 2022, and English translation, 2 pages.
German Patent Complaint Proceedings in the Regional Court, Mannheim, Germany, *Adare Development I, L.P. vs. Dr. Falk Pharma GmbH*, Docket No. 7 O 75/19, Official Order dated Feb. 12, 2020, and English translation, 5 pages.
German Patent Complaint Proceedings in the Regional Court, Mannheim, Germany, *Adare Development I, L.P. vs. Dr. Falk Pharma GmbH*, Docket No. 7 O 75/19, Official Order dated Feb. 13, 2020, and English translation, 3 pages.
German Patent Complaint Proceedings in the Regional Court, Mannheim, Germany, *Adare Development I, L.P. vs. Dr. Falk Pharma GmbH*, Docket No. 7 O 75/19, Pleadings as filed, dated Dec. 16, 2019, and English translation, 66 pages.
German Patent Complaint Proceedings in the Regional Court, Mannheim, Germany, *Adare Development I, L.P. vs. Dr. Falk Pharma GmbH*, Docket No. 7 O 75/19, Response to Rejoinder as filed, dated Feb. 6, 2020 (and English translation), 36 pages.
German Patent Complaint Proceedings in the Regional Court, Mannheim, Germany, *Adare Development I, L.P. vs. Dr. Falk Pharma GmbH*, Docket No. 7 O 75/19, Submission of Dr. Falk—rejoinder dated Jan. 30, 2020 (and English translation), 38 pages.

(56) References Cited

OTHER PUBLICATIONS

German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk—statement of defense, filed Oct. 7, 2019 (and English translation), 14 pages.
German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk dated Feb. 10, 2020, 6 pages, in German and English.
German Patent Complaint Proceedings in the Regional Court, Mannheim, Germany, *Adare Development I, L.P.* vs. *Dr. Falk Pharma GmbH*, Docket No. 7 O 75/19, Writ as filed, dated Feb. 11, 2020, and English translation, 5 pages.
German Patent Infringement Proceedings in the Regional Court, Mannheim, Germany, *Adare Development I, L.P.* vs. *Dr. Falk Pharma GmbH*, Docket No. 7 O 75/19, Patent Complaint dated Jul. 3, 2019, with English translation, 107 pages.
German Utility Model Cancellation Action, Request for Cancellation, filed by Dr. Falk Pharma GmbH on Mar. 1, 2019 with the German Patent Office, in connection with DE Patent No. 202010018594 U1 in the name of Adare Pharmaceuticals, Inc., and English translation, 21 pages.
German Utility Model Cancellation Proceedings DE 20201 018594 U1, *Dr. Falk Pharma GmbH* (Plaintiff/Respondent) vs. *Adare Pharmaceuticals US, L.P. / Ellodi Pharmaceuticals L.P.* (Patentee/Appellant), Statement of Grounds of Appeal dated Feb. 26, 2021 (and English translation), and Exhibit B817—Current EPA register extract on D5 dated Nov. 27, 2020, 117 pages.
German Utility Model Cancellation Proceedings, *Dr. Falk Pharma GmbH* (Plaintiff) vs. *Adare Development I, L.P.* (Patentee), Utility model DE 20201 018594 U1, Adare—Further Submission as filed dated Jul. 12, 2019, and English translation, 56 pages.
German Utility Model Cancellation Proceedings, *Dr. Falk Pharma GmbH* (Plaintiff) vs. *Adare Development I, L.P.* (Patentee), Utility model DE 20201 018594 U1, Auxiliary Request I-IV (marked-up) dated and as filed Jul. 1, 2020, and English translation, 17 pages.
German Utility Model Cancellation Proceedings, *Dr. Falk Pharma GmbH* (Plaintiff) vs. *Adare Development I, L.P.* (Patentee), Utility model DE 20201 018594 U1, Official Communication—Interlocutory Notice dated Jan. 22, 2020 (and English translation), 12 pages.
German Utility Model Cancellation Proceedings, *Dr. Falk Pharma GmbH* (Plaintiff) vs. *Adare Development I, L.P.* (Patentee), Utility model DE 20201 018594 U1, Response to Dr. Falk and Summons dated Jul. 2, 2020, and English translation, 18 pages.
German Utility Model Cancellation Proceedings, *Dr. Falk Pharma GmbH* (Plaintiff) vs. *Adare Development I, L.P.* (Patentee), Utility model DE 20201 018594 U1, Response to Pleadings as filed dated Oct. 17, 2019, and English translation, 25 pages.
German Utility Model Cancellation Proceedings, *Dr. Falk Pharma GmbH* (Plaintiff) vs. *Adare Development I, L.P.* (Patentee), Utility model DE 20201 018594 U1, Submission of Dr. Falk—Pleadings dated Sep. 13, 2019 (and English translation), 27 pages.
German Utility Model Cancellation Proceedings, *Dr. Falk Pharma GmbH* (Plaintiff) vs. *Adare Development I, L.P.* (Patentee), Utility model DE 202010018594 U1, Adare's Response dated Apr. 6, 2020 to Interlocutory Decision, and English translation, 29 pages.
German Utility Model Cancellation Proceedings, *Dr. Falk Pharma GmbH* (Plaintiff) vs. *Adare Development I, L.P.* (Patentee), Utility model DE 202010018594 U1, Communication from Adare to German Patent Office, Auxiliary Requests 1 and 2 (clean, marked-up and English translations) as filed Apr. 6, 2020, 23 pages.
German Utility Model Cancellation Proceedings, *Dr. Falk Pharma GmbH* (Plaintiff) vs. *Adare Development I, L.P.* (Patentee), Utility model DE 202010018594 U1, Submission of Dr. Falk—response to Adare and summons, dated Jul. 8, 2020 (and English translation), 11 pages.
German Utility Model Cancellation Proceedings, *Dr. Falk Pharma GmbH* (Plaintiff) vs. *Adare Development I, L.P.* (Patentee), Utility model DE 202010018594 U1, submission/Response by Dr. Falk Pharma GmbH dated Apr. 8, 2020 (and English translation), 18 pages.
Hahm and Augsburger, Orally Disintegrating Tablets and Related Tablet Formulations, Pharmaceutical Dosage Forms: Tablets, Third Edition, Ch. 9, vol. 2, Herausgeber: (eds) Larry L. Augsburger, Stephen W. Hoag, CRC Press (2008), 21 pages.
Ham, et al., "Quantitation of esophagal transit by means of 81mKr." European Journal of Nuclear Medicine (1984); 9: 362-365.
Handbook of Pharmaceutical Excipients (2009); Sixth Edition, ISBN 978 1 58212 135 2, (eds.) Rowe, et al., Cover Page, Print/Copyright and Preface Pages, 4 pages.
International Preliminary Report on Patentability for International Application No. PCT/US2017/047474, dated Feb. 19, 2019, 8 pages.
Jorveza (budesonide) Update by the Committee for Medicinal Products for Human Use (CHMP), Summary of opinion1 (post authorisation) dated Mar. 26, 2020, European Medicines Agency, 1 page.
Katdare and Chaubal (eds)., Excipient Development for Pharmaceutical, Biotechnology and Drug Delivery Systems, Herausg. CRC Press, Taylor & Francis Group, Boca Raton, USA, 2006; dart: Excipients for Oral Liquid Formulations, S. 155-180, 28 pages.
Khan and Orenstein, "Eosinophilic Gastroenteritis: Epidemiology, Diagnosis and Management." Paediatr Drugs. (2002); 4(9): 563-570.
Koukourakis, et al., "Oral Administration of Recombinant Human Granulocyte Macrophage Colony-stimulating Factor in the Management of Radiotherapy-induced Esophagitis", Clinical Cancer Research (Dec. 1999); 5(12): 3970-3976.
Krishna, et al., "Treatment of Eosinophilic Esophagitis is Oral Viscous Budesonide Superior to Swallowed Fluticasone Spray?" Gastroenterol Hepatol (Jan. 2011); 7(1): 55-59.
Kumari and Rajendran, "Effect of topical nasal steroid spray in the treatment of non-specific recurrent/chronic pharyngitis—a trial study." Indian Journal of Otolaryngology and Head & Neck Surgery, 60(3): 199-201 (2008).
Langdon, BA and Mullamey, (2006) Handbook of Pharmaceutical Excipients. (eds.) Rowe, R.C., Sheskey, PJ and Owen, S.C., London: Pharmaceutical Press and American Pharmacists Association (extract—pp. 53-55 and 742-743), 14 pages.
Lee, Geoffrey, Professor, Report of Professor Geoffrey Lee, Ph.D. on measurement of disintegration time of "Jorveza 1 mg orodispersible tablet" dated Nov. 15, 2019, 16 pages.
Li, Xiaowei, et al., "Advances in Injectable Thermosensitive Polymers". Polymer Bulletin, No. 3, pp. 109-115, Jun. 30, 2015 (with English Abstract), 7 pages.
Liacouras, et al., "Primary Eosinophilic Esophagitis in Children: Successful Treatment with Oral Corticosteroids". Journal of Pediatric Gastroenterology & Nutrition (1998); 26(4): 380-385.
Mahmoudi et al. "Effect of drug particle size on blend segregation and content uniformity". Contributed poster, AAPS Annual Meeting (USA) 2010, 1 page. (non-English).
Mahmoudi et al. "Influence of filler in blend uniformity of micronized drugs". Contributed poster, AAPS Annual Meeting (USA) 2010, 1 page.
Malaysian Application No. PI 2012001434, Search Report dated Jan. 29, 2016, 1 page.
Martin, et al., "Pediatric Eosinophilic Esophagitis Symptom Scores (PEESS® v2.0) identify histologic and molecular correlates of the key clinical features of disease". J Allergy Clin Immunol. (Jun. 2015); 135(6): 1519-1528.e8.
McGinity, J. W., et al. "Dissolution and uniformity properties of ordered mixes of micronized griseofulvin and a directly compressible excipient." Drug Development and Industrial Pharmacy, 11(4): 891-900 (1985).
Merck Index, "Budesonide," 14th Edition, p. 240 (2006).
Merck Index, "Ciclesonide," 14th Edition, p. 376 (2006).
Merck Index, "Clotrimazole," 14th Edition, p. 407 (2006).
Merck Index, "Mometasone Furoate," 14th Edition, pp. 1077-1078 (2006).
Merck Index, "Voriconazole," 14th Edition, p. 1728 (2006).

(56) References Cited

OTHER PUBLICATIONS

Miehlke, et al., "A randomised, double-blind trial comparing budesonide formulations and dosages for short-term treatment of eosinophilic oesophagitis", Gut (2016); 65: 390-399.
Moreton, R. Christian, "Disintegrants in Tableting". In book: Pharmaceutical Dosage Forms: Tablets, vol. 2, Herausgeber Augsburger & Hoag, CRC Press, Taylor and Francis Group (2008); Ch. 6, pp. 217-249, 33 pages.
New World Encyclopedia, "Gastrointestinal tract", https://web.archive.org/web/20090917122455/https://www.newworldencyclopedia.or . . . , Jul. 8, 2019, 7 pages.
New World Encyclopedia, "Gastrointestinal tract", https://www.newworldencyclopedia.org/entry/Gastrointestinal_tract, Jul. 8, 2019, 6 pages.
Nishimura, S., et al. "Factors associated with esophageal candidiasis and its endoscopic severity in the era of antiretroviral therapy." PLoS One (2013); 8(3): e58217, 6pgs.
Novopulmon E Novolizer, Instructions for the medical use of the medicament, [Instrukciya po medicinskomu primeneniyu preparata Novopulmon Novolizer (international nonproprietary name: budesonide), registracionniy nomer N LS-002405-231211, 23.12.2011], MEDA Manufacturing, GmbH Registration No. LS-002405, Date of Registration Dec. 23, 2011 (with English summary of relevant portions), 9 pages.
"NUROFEN" tablet package insert, 200 MG Tablets and Capsules, Date of revision: Feb. 2018, Reference ID 3039860, and English version, 2 pages.
Opposition Proceedings in European Patent No. 2886108 (Appln. No. 13199278.6), filed by Adare Development, I, L.P on Nov. 6, 2019, EPO Communication dated Apr. 6, 2021, enclosing Patentee's Response to Submissions dated Mar. 30, 2021, and English translation, 9 pages.
Opposition Proceedings in European Patent No. EP 2482822 (Appln. No. 10821232.5), filed by Dr. Falk Pharma GmbH on Mar. 1, 2019; Appeal No. T1954/21-3.3.01 dated Jan. 4, 2022, 20 pages.
Opposition Proceedings in European Patent No. EP 2886108 (Appln. No. 13199278.6), filed by Ellodi Pharmaceuticals, L.P., on Nov. 6, 2019, Interlocutory Decision dated Jan. 5, 2022, and English translation, 43 pages.
Opposition Proceedings in European Patent No. EP 2886108 (Appln. No. 13199278.6), filed by Ellodi Pharmaceuticals, L.P., on Nov. 6, 2019, Minutes of Oral Proceedings dated Jan. 5, 2022, and English translation, 25 pages.
Opposition Proceedings in European Patent No. EP 3041476 (Appln. No. 14842811.3), filed by Dr. Falk Pharma GmbH on Jul. 22, 2020; EPO's Communication dated Nov. 18, 2021 enclosing Opponent's, Dr. Falk Pharma GmbH's Further Submissions dated Nov. 15, 2021, and English translation, 21 pages.
Opposition Proceedings in European Patent No. EP 3041476 (Appln. No. 14842811.3), filed by Dr. Falk Pharma GmbH on Jul. 22, 2020; Interlocutory Decision dated Feb. 14, 2022, 61 pages.
Opposition Proceedings in European Patent No. EP 3041476 (Appln. No. 14842811.3), filed by Dr. Falk Pharma GmbH on Jul. 22, 2020; Minutes of Oral Proceedings dated Feb. 14, 2022, 15 pages.
Opposition Proceedings in European Patent No. 2482822 (Appln. No. 10821232.05), filed by Dr. Falk Pharma GmbH on Mar. 1, 2019, D18—Dr F's novelty table 2020, 2 pages.
Opposition Proceedings in European Patent No. 2482822 (Appln. No. 10821232.05), filed by Dr. Falk Pharma GmbH on Mar. 1, 2019, EPO Communication—communication of notice of opposition dated May 13, 2019, 1 page.
Opposition Proceedings in European Patent No. 2482822 (Appln. No. 10821232.05), filed by Dr. Falk Pharma GmbH on Mar. 1, 2019, EPO Communication dated Nov. 5, 2019, enclosing Opponent's Further Written Submissions dated/filed on Oct. 29, 2019 (and English translation) including consolidated list of prior art, 29 pages.
Opposition Proceedings in European Patent No. 2482822 (Appln. No. 10821232.05), filed by Dr. Falk Pharma GmbH on Mar. 1, 2019, EPO Communication dated Sep. 26, 2019, transmitting Adare's submission filed Sep. 20, 2019, 88 pages.
Opposition Proceedings in European Patent No. 2482822 (Appln. No. 10821232.05), filed by Dr. Falk Pharma GmbH on Mar. 1, 2019, Notice of Opposition dated Mar. 1, 2019, and English translation, 23 pages.
Opposition Proceedings in European Patent No. 2482822 (Appln. No. 10821232.05), filed by Dr. Falk Pharma GmbH on Mar. 1, 2019, Patentee, Adare Development I, L.P.'s Response dated Dec. 16, 2019 in response to further submissions filed by Dr. Falk Pharma GmbH on Oct. 29, 2019, 16 pages.
Opposition Proceedings in European Patent No. 2482822 (Appln. No. 10821232.05), filed by Dr. Falk Pharma GmbH on Mar. 1, 2019, Submission filed by Adare Development I, L.P., on Sep. 20, 2019, 91 pages.
Opposition Proceedings in European Patent No. 2482822 (Appln. No. 10821232.5), filed by Dr. Falk Pharma GmbH on Mar. 1, 2019, EPO Communication dated Nov. 5, 2019, forwarding Letter from Opponent dated Oct. 29, 2019, 247 pages.
Opposition Proceedings in European Patent No. 2886108 (Appln. No. 13199278.6), filed by Adare Development, I, L.P on Nov. 6, 2019, Consolidated List of Cited Opposition Documents, 1 page.
Opposition Proceedings in European Patent No. 2886108 (Appln. No. 13199278.6), filed by Adare Development, I, L.P on Nov. 6, 2019, EPO Communication dated Jul. 24, 2020 regarding oral proceedings, 6 pages.
Opposition Proceedings in European Patent No. 2886108 (Appln. No. 13199278.6), filed by Adare Development, I, L.P on Nov. 6, 2019, EPO Communication dated Mar. 25, 2020 transmitting communication from Dr. Falk Pharma GmbH dated Mar. 20, 2020, and English translation, 34 pages.
Opposition Proceedings in European Patent No. 2886108 (Appln. No. 13199278.6), filed by Adare Development, I, L.P on Nov. 6, 2019, EPO Communication re Summons to Attend Oral Proceedings and Preliminary Opinion, dated Jul. 2, 2020, and English translation, 18 pages.
Opposition Proceedings in European Patent No. 2886108 (Appln. No. 13199278.6), filed by Ellodi Pharmaceuticals, L.P., on Nov. 6, 2019, Adare's Written Submissions in Preparation for Oral Proceedings on Apr. 23, 2021, dated Feb. 23, 2021, 25 pages.
Opposition Proceedings in European Patent No. 3086782 (Appln. No. 14814872.9), filed by Adare Development, I, L.P on Jun. 26, 2019, EPO Communication dated Jul. 2, 2019, transmitting Notice of Opposition filed Jun. 26, 2019, 43 pages.
Opposition Proceedings in European Patent No. 3086782 (Appln. No. 14814872.9), filed by Adare Development, I, L.P on Jun. 26, 2019, EPO Communication dated Jul. 22, 2020 regarding date of oral proceedings, 3 pages.
Opposition Proceedings in European Patent No. 3086782 (Appln. No. 14814872.9), filed by Adare Development, I, L.P on Jun. 26, 2019, EPO Communication dated Nov. 19, 2019, with Patentee's response to Opposition dated Nov. 8, 2019, and English translation, 22 pages.
Opposition Proceedings in European Patent No. 3086782 (Appln. No. 14814872.9), filed by Adare Development, I, L.P on Jun. 26, 2019, EPO Communication to Adare regarding oral proceedings dated Mar. 2, 2020, and English translation, 14 pages.
Opposition Proceedings in European Patent No. 3086782 (Appln. No. 14814872.9), filed by Adare Development, I, L.P on Jun. 26, 2019, Patentee, Dr. Falk's Written Submissions, Auxiliary Request I and Test Report Jorveza® 1 mg (dated Aug. 18, 2020, produced by Patentee, Dr. Falk Pharma), filed Sep. 10, 2020, and English translation, 22 pages.
Opposition Proceedings in European Patent No. EP 2482822, Appeal No. T1954/21-3.3.01 (Appln. No. 10821232.5), filed by Dr. Falk Pharma GmbH on Mar. 1, 2019; communication from the European Patent Office (EPO) dated May 18, 2022 enclosing Opponent's response to appeal dated May 12, 2022 and D27, and English translation, 44 pages.
Opposition Proceedings in European Patent No. EP 2482822, Appeal No. T1954/21-3.3.01 (Appln. No. 10821232.5), filed by Dr. Falk Pharma GmbH on Mar. 1, 2019; Ellodi's Withdrawal of Appeal dated Jul. 11, 2022, 3 pages.

(56) References Cited

OTHER PUBLICATIONS

Opposition Proceedings in European Patent No. EP 2482822, Appeal No. T1954/21-3.3.01 (Appln. No. 10821232.5), filed by Dr. Falk Pharma GmbH on Mar. 1, 2019; EPO's Communication—Minutes of Oral Proceeding, dated Aug. 25, 2021, and English translation, 11 pages.
Opposition Proceedings in European Patent No. EP 2482822 (Appln. No. 1082123205), filed by Dr. Falk Pharma GmbH on Mar. 1, 2019, Adare—Letter to EPO re Oral Proceedings dated Jul. 17, 2020, 5 pages.
Opposition Proceedings in European Patent No. EP 2482822 (Appln. No. 1082123205), filed by Dr. Falk Pharma GmbH on Mar. 1, 2019; Adare's Communication to the EPO re oral proceedings, dated Aug. 11, 2020, 4 pages.
Opposition Proceedings in European Patent No. EP 2482822 (Appln. No. 1082123205), filed by Dr. Falk Pharma GmbH on Mar. 1, 2019; EPO Communication dated Jul. 23, 2020, with Written Submission from Adare (Proprietor) dated Jul. 17, 2020, 126 pages.
Opposition Proceedings in European Patent No. EP 2482822 (Appln. No. 1082123205), filed by Dr. Falk Pharma GmbH on Mar. 1, 2019, EPO Communication dated Mar. 8, 2019 regarding notice of opposition, 1 page.
Opposition Proceedings in European Patent No. EP 2482822 (Appln. No. 1082123205), filed by Dr. Falk Pharma GmbH on Mar. 1, 2019; EPO's Communication re oral proceedings, dated Aug. 5, 2020, 1 page.
Opposition Proceedings in European Patent No. EP 2482822 (Appln. No. 1082123205), filed by Dr. Falk Pharma GmbH on Mar. 1, 2019, EPO Communication re Oral Proceedings dated Jul. 13, 2020, 3 pages.
Opposition Proceedings in European Patent No. EP 2482822 (Appln. No. 1082123205), filed by Dr. Falk Pharma GmbH on Mar. 1, 2019; EPO's consolidated list of cited opposition documents, Jul. 18, 2020, 1 page.
Opposition Proceedings in European Patent No. EP 2482822 (Appln. No. 1082123205), filed by Dr. Falk Pharma GmbH on Mar. 1, 2019, Summons to Attend Oral Hearing and Preliminary Opinion in opposition dated Feb. 13, 2020, 15 pages.
Opposition Proceedings in European Patent No. EP 2482822 (Appln. No. 1082123205), filed by Dr. Falk Pharma GmbH on Mar. 1, 2019, Summons to attend oral proceedings dated Feb. 13, 2020, 13 pages.
Opposition Proceedings in European Patent No. EP 2482822 (Appln. No. 1082123205), filed by Dr. Falk Pharma GmbH on Mar. 1, 2019; Written Submissions of the Patentee in Preparation for Oral Proceedings on Mar. 8, 2021, dated Jan. 8, 2021, with Auxiliary Requests 1-14, 52 pages.
Opposition Proceedings in European Patent No. EP 2482822 (Appln. No. 10821232.5), filed by Dr. Falk Pharma GmbH on Mar. 1, 2019; EPO Communication in connection with Summons to attend oral proceedings, dated Nov. 20, 2020, 12 pages.
Opposition Proceedings in European Patent No. EP 2482822 (Appln. No. 10821232.5), filed by Dr. Falk Pharma GmbH on Mar. 1, 2019; Falk's Communication to the EPO re oral proceedings, dated Aug. 12, 2020, 3 pages.
Opposition Proceedings in European Patent No. EP 2482822 (Appln. No. 10821232.5), filed by Dr. Falk Pharma GmbH on Mar. 1, 2019, Opponent's response to Summons dated Jul. 17, 2020, and English translation, 15 pages.
Opposition Proceedings in European Patent No. EP 2482822 (Appln. No. 10821232.5), filed by Dr. Falk Pharma GmbH on Mar. 1, 2019; Opponent's submissions dated Mar. 1, 2021, and English translation, 11 pages.
Opposition Proceedings in European Patent No. EP 2482822 (Appln. No. 10821232.5), filed by Dr. Falk Pharma GmbH on Mar. 1, 2019; Written Submissions of the Opponent in response to the Summons to attend Oral Proceedings, dated and filed Dec. 8, 2020, and English translation, 37 pages.
Opposition Proceedings in European Patent No. EP 2886108, Appeal No. T0611/22-3.3.07 (Appln. No. 13199278.6), (in the name of Dr. Falk Pharma GmbH) filed by Ellodi Pharmaceuticals, L.P. on Nov. 6, 2019; EPO Communication dated May 27, 2022 confirming Termination of Appeal Proceedings filed May 16, 2022, 4 pages.
Opposition Proceedings in European Patent No. EP 2886108 (Appln. No. 13199278.6), filed by Adare Development I, L.P., on Nov. 6, 2019, Dr. Falk Pharma's Response to Summons and Adare's Written Submissions and clean and marked versions of Auxiliary Requests I and II, dated Dec. 18, 2020, and English translation, 26 pages.
Opposition Proceedings in European Patent No. EP 2886108 (Appln. No. 13199278.6), filed by Ellodi Pharmaceuticals, L.P., on Nov. 6, 2019, Datasheet for the decision of Oct. 14, 2019, Case Number T 1621/16-3.3.06, Application No. 09163237.2, 28 pages.
Opposition Proceedings in European Patent No. EP 2886108 (Appln. No. 13199278.6), filed by Ellodi Pharmaceuticals, L.P., on Nov. 6, 2019, Ellodi's Notice of Appeal against decision filed Mar. 4, 2022, 5 pages.
Opposition Proceedings in European Patent No. EP 2886108 (Appln. No. 13199278.6), filed by Ellodi Pharmaceuticals, L.P., on Nov. 6, 2019, Ellodi's Withdrawal of Appeal filed May 16, 2022, 3 pages.
Opposition Proceedings in European Patent No. EP 3041476, Appeal No. T1007/22-3.3.07 (Appln. No. 14842811.3), filed by Dr. Falk Pharma GmbH on Jul. 22, 2020; EPO Communication dated Jul. 22, 2022 confirming withdrawal of appeal as filed Jul. 14, 2022 by Opponent, 4 pages.
Opposition Proceedings in European Patent No. EP 3041476, Appeal No. T1007/22-3.3.07 (Appln. No. 14842811.3), filed by Dr. Falk Pharma GmbH on Jul. 22, 2020; EPO Communication dated Jun. 20, 2022 enclosing Opponent's Grounds of Appeal dated Jun. 10, 2022, and English translation, 27 pages.
Opposition Proceedings in European Patent No. EP 3041476, Appeal No. T1007/22-3.3.07 (Appln. No. 14842811.3), filed by Dr. Falk Pharma GmbH on Jul. 22, 2020; Withdrawal of Appeal filed by Ellodi Pharmaceuticals, L.P. dated Jun. 14, 2022, 3 pages.
Opposition Proceedings in European Patent No. EP 3041476 (Appln. No. 14842811.3), filed by Dr. Falk Pharma GmbH on Jul. 22, 2020; EPO Communication dated Feb. 22, 2021 enclosing Opponent's Submissions (and English translation), dated Feb. 16, 2021, 11 pages.
Opposition Proceedings in European Patent No. EP 3041476 (Appln. No. 14842811.3), filed by Dr. Falk Pharma GmbH on Jul. 22, 2020; EPO Communication dated Jul. 29, 2020 advising of and enclosing Notice of Opposition filed by Dr. Falk Pharma GmbH on Jul. 22, 2020, 82 pages.
Opposition Proceedings in European Patent No. EP 3041476 (Appln. No. 14842811.3), filed by Dr. Falk Pharma GmbH on Jul. 22, 2020; Notice of Appeal filed by Ellodi Pharmaceuticals, L.P. dated Apr. 22, 2022, 5 pages.
Opposition Proceedings in European Patent No. EP 3041476 (Appln. No. 14842811.3), filed by Dr. Falk Pharma GmbH on Jul. 22, 2020; Notice of Opposition and Statement of Grounds of Opposition (with English translation of Statement of Grounds of Opposition), and Consolidated List of references relied upon, filed Jul. 22, 2020, 513 pages.
Opposition Proceedings in European Patent No. EP 3041476 (Appln. No. 14842811.3), filed by Dr. Falk Pharma GmbH on Jul. 22, 2020; Patentee Adare's Response to Opposition dated .Jan. 11, 2021, 15 pages.
Opposition Proceedings in European Patent No. EP 3041476 (Appln. No. 14842811.3), filed by Dr. Falk Pharma GmbH on Jul. 22, 2020; Patentee Ellodi Pharmaceuticals, L.P.'s Written Submission in Preparation for Oral Proceedings on Dec. 8, 2021 with new Auxiliary Requests 1-3, dated Oct. 8, 2021, 51 pages.
Opposition Proceedings in European Patent No. EP 3403654 (Appln. No. 18178891.0), filed by Dr. Falk Pharma GmbH; Adare's Response to the Grounds of Opposition, filed Nov. 2, 2020, 78 pages.
Opposition Proceedings in European Patent No. EP 3403654 (Appln. No. 18178891.0), filed by Dr. Falk Pharma GmbH; Consolidated List of References dated and filed Dec. 8, 2020, 1 page.
Opposition Proceedings in European Patent No. EP 3403654 (Appln. No. 18178891.0), filed by Dr. Falk Pharma GmbH; EPO Communication of a notice of opposition dated Jun. 22, 2020, 1 page.

(56) References Cited

OTHER PUBLICATIONS

Opposition Proceedings in European Patent No. EP 3403654 (Appln. No. 18178891.0), filed by Dr. Falk Pharma GmbH; EPO Communication of a notice of opposition dated May 8, 2020, 1 page.
Opposition Proceedings in European Patent No. EP 3403654 (Appln. No. 18178891.0), filed by Dr. Falk Pharma GmbH; Opponent's Further Written Submissions dated and filed Dec. 8, 2020, and English translation, 30 pages.
Opposition Proceedings in European Patent No. EP 3403654 (Appln. No. 18178891.0), filed by Dr. Falk Pharma GmbH; Opponent's Submission/Withdrawal of Opposition dated Jul. 20, 2022, and English translation, 2 pages.
Opposition Proceedings in European Patent No. EP 3403654 (Appln. No. 18178891.0), filed by Dr. Falk Pharma GmbH; Statement of Grounds of Opposition filed on Apr. 28, 2020, and English translation, 38 pages.
Patent Complaint Proceedings in the Regional Court, Mannheim, Germany, *Adare Development I, L.P.* vs. *Dr. Falk Pharma GmbH*, Reference No. 4c O Oct. 2019, Decision (and English translation) dated Oct. 26, 2020, pronounced in the oral hearing of Jul. 21, 2020, 45 pages.
PCT Application No. PCT/US2010/050860, International Preliminary Report on Patentability dated Apr. 3, 2012.
PCT Application No. PCT/US2010/050860, International Search Report dated Feb. 10, 2011.
PCT Application No. PCT/US2010/050860, Written Opinion of the International Search Authority dated Feb. 10, 2011.
PCT Application No. PCT/US2014/052073, International Preliminary Report on Patentability dated Mar. 8, 2016.
PCT Application No. PCT/US2014/052073, International Search Report dated Nov. 20, 2014.
PCT Application No. PCT/US2014/052073, Written Opinion of the International Searching Authority dated Nov. 20, 2014.
PCT Application No. PCT/US2014/054203, International Preliminary Report on Patentability dated Mar. 8, 2016.
PCT Application No. PCT/US2014/054203, International Search Report dated Dec. 23, 2014.
PCT Application No. PCT/US2014/054203, Written Opinion of the International Searching Authority dated Dec. 23, 2014.
PCT Application No. PCT/US2019/019040, International Preliminary Report on Patentability, dated Aug. 27, 2020, 8 pages.
PCT Application No. PCT/US2019/019040, International Search Report and Written Opinion, mailed Jun. 25, 2019, 12 pages.
PCT Application No. PCT/US2019/019040, Invitation to Pay Additional Fees, mailed Apr. 25, 2019, 2 pages.
PCT/US2020/053778, International Preliminary Report on Patentability mailed Apr. 5, 2022, 7 pages.
PCT/US2020/053778, International Search Report and Written Opinion mailed Jan. 8, 2021, 9 pages.
PCT/US2021/042566, International Search Report and Written Opinion, mailed Nov. 5, 2021, 9 pages.
Pelle, et al., "Using defined daily doses to study the use of antibacterials in UK hospitals". Hosp Pharm (2006); 13: 133-136.
Ponchel, Gilles, "Formulation of oral mucosal drug delivery systems for the systemic delivery of bioactive materials". Advanced Drug Delivery Reviews, vol. 13, Issues 1-2, Jan.-Feb. 1994, pp. 75-87.
Ratnaparkhi, et al., "Review On: Fast Dissolving Tablet", Journal of Pharmacy Research. (Jan. 2009); 2(1): 5-12.
Remedios, et al., "Eosinophilic esophagitis in adults: clinical, endoscopic, histologic findings, and response to treatment with fluticasone propionate". Gastrointestinal Endoscopy (2006); 63(1): 3-12.
Robertson, et al., "Oesophageal transit of small tablets", J. Pharm. Pharmacol. (1988); 40: 595-596.
Schaefer, et al., "Comparison of Oral Prednisone and Topical Fluticasone in the Treatment of Eosinophilic Esophagitis: A Randomized Trial in Children". Clinical Gastroenterology and Hepatology (2008); 6: 165-173.

Schoepfer, et al., "Development and validation of a symptom-based activity index for adults with eosinophilic esophagitis". Gastroenterology (Dec. 1, 2014); 147(6): 1255-1266.
Singh, Arun, et al. "Oral candidiasis: An overview." Journal of Oral and Maxillofacial Pathology: JOMFP (2014); 18.Suppl 1: S81.
Sjostrom and Cairncross, "What Makes Flavor Leadership." Food Technology (1953); (7) 2: 56-58.
Supplementary European Search Report in European Patent Application No. EP 20192973.4, dated Nov. 18, 2020, 5 pages.
Taft, et al., "The adult eosinophilic oesophagitis quality of life questionnaire: a new measure of health-related quality of life". Alimentary Pharmacology & Therapeutics (Oct. 2011); 34(7): 790-798.
Taiwanese Application No. TW 099133628, Search Report (English translation) dated Nov. 16, 2014, 9 pages.
Taiwanese Application No. TW 104107443, Search Report (English translation) dated May 29, 2015,1 page.
Takaku, Fumimaro, et al. Manual of Therapeutic Agents 2007, Published 2007, p. 617-619 (and English translation/summary of pertinent paragraphs), 5 pages.
Tayebi and Mortazavi, "Formulation and Evaluation of a Novel Matrix-Type Orally Disintegrating Ibuprofen Tablet". Iran J Pharm Res. (2011 Summer); 10(3): 469-479.
Teitelbaum et al. "Eosinophilic esophagitis in children: immunopathological analysis and response to fluticasone propionate." Gastroenterology (2002), 122(5): 1216-1225.
Thorburn and Ferguson, "Topical corticosteroids and lesions of the oral mucosa". Advanced Drug Delivery Reviews, vol. 13, Issues 1-2, Jan.-Feb. 1994, pp. 135-149.
UM Complaint Proceedings in the Regional Court, Mannheim, Germany, *Adare Development I, L.P.* vs. *Dr. Falk Pharma GmbH*, Reference No. 4c O Oct. 2019, Replica dated Jul. 19, 2019, and English translation, 25 pages.
UM Complaint Proceedings in the Regional Court, Mannheim, Germany, *Adare Development I, L.P.* vs. *Dr. Falk Pharma GmbH*, Complaint dated Jul. 3, 2019, and English translation, 34 pages.
UM Complaint Proceedings in the Regional Court, Mannheim, Germany, *Adare Development I, L.P.* vs. *Dr. Falk Pharma GmbH*, Reference No. 4c O Oct. 2019, submission by Dr. Falk Pharma GmbH—statement of defense, dated May 24, 2019, and English translation, 16 pages.
UM Complaint Proceedings in the Regional Court, Mannheim, Germany, *Adare Development I, L.P.* vs. *Dr. Falk Pharma GmbH*, Reference No. 4c O Oct. 2019, Submission of Dr. Falk—Rejoinder dated Sep. 13, 2019 (English translation), 8 pages.
UM Complaint Proceedings in the Regional Court, Mannheim, Germany, *Ellodi Pharmaceuticals, L.P. (formerly Adare Development I, L.P.)* vs. *Dr. Falk Pharma GmbH*, Reference No. 4c O Oct. 2019, Defendant's Consent to Withdrawal filed Jul. 15, 2022, and English translation, 2 pages.
UM Complaint Proceedings in the Regional Court, Mannheim, Germany, *Ellodi Pharmaceuticals, L.P. (formerly Adare Development I, L.P.)* vs. *Dr. Falk Pharma GmbH*, Reference No. 4c O Oct. 2019, Order concerning value under dispute dated Jul. 20, 2022, and English translation, 2 pages.
UM Complaint Proceedings in the Regional Court, Mannheim, Germany, *Ellodi Pharmaceuticals, L.P. (formerly Adare Development I, L.P.)* vs. *Dr. Falk Pharma GmbH*, Reference No. 4c O Oct. 2019, Withdrawal Submission filed by Ellodi Pharmaceuticals, L.P., dated Jul. 11, 2022, and English translation, 2 pages.
Utility Model Cancellation Proceedings, *Dr. Falk Pharma GmbH* (Plaintiff) vs. *Adare Development I, L.P.* (Patentee), Utility model DE 202010018594 U1, Jul. 12, 2019—Exhibit BB1 "Breakdown of Features", and English translation, 2 pages.
Utility Model Cancellation Proceedings, *Dr. Falk Pharma GmbH* (Plaintiff) vs. *Adare Development I, L.P.* (Patentee), Utility model DE 202010018594 U1, Jul. 12, 2019—Exhibit BB4—Letter from Lederer & Keller dated Sep. 27, 2018 regarding European Patent No. 2211896, and Machine English translation, 28 pages.
Vogt et al., "Biowaiver monographs for immediate release solid oral dosage forms: Prednisolone," Journal of Pharmaceutical Sciences, 96(1): 27-37 (2007).

(56) References Cited

OTHER PUBLICATIONS

Von Arnim and Malfertheiner, "Eosinophilic Esophagitis—Treatment of Eosinophilic Esophagitis with Drugs: Corticosteroids", Digestive Diseases (2014); 32: 126-129.
Webb, Paul A., "Surface Area, Porosity, and Related Physical Characteristics". In book: Pharmaceutical Dosage Forms: Tablets, 3rd Edition, vol. 3, CRC Press, Taylor and Francis Group, Boca Raton, London, New York (2008); Chapter 11, pp. 277-302.
Wechsler, Joshua B., et al. "Eosinophilic esophagitis reference score accurately identifies disease activity and treatment effects in children." Clinical Gastroenterology and Hepatology (2018); 16(7): 1056-1063.
Wei et al., "Efficacy of Single-Dose Dexamethasone as Adjuvant Therapy for Acute Pharyngitis" The Laryngoscope, 112(1):87-93 (2002).
Wen, Hong, (ed. Swarbick, James) "Adsorption at Solid Surfaces: Pharmaceutical Applications". Encyclopedia of Pharmaceutical Technology, Third Edition, vol. 1 (2007); pp. 34-38, 7 pages.
Wikipedia, "Retard", https://de.wikipedia.org/wiki/Retard, Jun. 13, 2019, and Google machine translation, 7 pages.
Yalkowsky and Bolton. "Particle size and content uniformity." Pharmaceutical Research, 7(9): 962-966 (1990).
Budenofalk®, Budenofalk® 3mg, Dr. Falk Pharma GMBH, Brochure (6th Revised Edition 2005), 136 pages.
Budenofalk®, Budesonide Budenofalk® 3mg, First-line-corticosteroid, Dr. Falk Pharma GMBH, Advertisement (2007), 1 page.
Curriculum Vitae of Alan F. Parr, Pharm.D., Ph.D., filed Jul. 22, 2024 in Petition for Inter Partes Review of U.S. Pat. No. 8,771,729 filed Jul. 22, 2024, 12 pages.
Danckwerts, M.D., "Intraoral Drug Delivery: A Comparative Review," American Journal of Drug Delivery (Sep. 2003); 1(3): 171-186.
Declaration of Alan F. Parr, Pharm.D., Ph.D., in Support of Petition for Inter Partes Review of U.S. Pat. No. 8,771,729 dated Apr. 17, 2024, filed Jul. 22, 2024, 174 pages.
Dr. Falk Pharma, "Where medicine and pharmaceuticals meet—a tried and trusted link", Dr. Falk Pharma GmbH, Brochure (2008), 29 pages.
"DRAFT Guidance: Guidance for Industry: Orally Disintegrating Tablets," U.S. Department of Health and Human Services, Food & Drug Administration, Center for Drug Evaluation and Research (CDER), Apr. 2007, 6 pages.
Elsing et al., "Budesonide for the treatment of obstructive eosinophilic jejunitis," Z. Gastroenterology Feb. 2007; 45(2): 187-189.
Faubion Jr., et al., "Treatment of eosinophilic esophagitis with inhaled corticosteroids". Journal of Pediatric Gastroenterology and Nutrition. Jul. 1, 1998; 27(1): 90-93, 6 pages.
Fu et al., "Orally fast disintegrating tablets: developments, technologies, taste-masking and clinical studies," Critical Reviews in Therapeutic Drug Carrier Systems (2004); 21(6): 433-475.
Goodman & Gilman's: The Pharmacological Basis of Therapeutics, 11th edition, eds. Brunton, Lazo, Parker, 2006, Ch. 38, pp. 1014-1015, pp. 1246-1256, 15 pages.
"Guidance for Industry: Orally Disintegrating Tablets," U.S. Department of Health and Human Services, Food & Drug Administration, Center for Drug Evaluation and Research (CDER), Dec. 2008, 6 pages.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Petition for Inter Partes Review of U.S. Pat. No. 8,771,729, dated and filed Jul. 22, 2024, including Exhibits and Petitioner Power of Attorney dated Mar. 24, 2024, 1079 pages.
International Preliminary Report on Patentability for International Application No. PCT/US2022/025297 dated Nov. 2, 2023, 8 pages.
Kolkman et al., "Evaluation of oral budesonide in the treatment of active distal ulcerative colitis," Drugs of Today Jul. 2004; 40(7): 589-601.

Noel et al., "Clinical and immunopathologic effects of swallowed fluticasone for eosinophilic esophagitis," Clinical Gastroenterology and Hepatology Jul. 2004; 2(7): 568-575.
Notice of Publication of FDA Guidance for Industry on Orally Disintegrating Tablets, Federal Register, vol. 73, No. 242 at 76366, Dec. 16, 2008, 1 page.
Opposition Proceedings in European Patent No. 2482822 B1 (Appln. No. 10821232.5), filed by Dr. Falk Pharma GmbH on Mar. 1, 2019, Adare Development I, L.P.'s (now Ellodi Pharmaceuticals, L.P.) Response to Grounds of Opposition dated Sep. 20, 2019, 27 pages.
Opposition Proceedings in European Patent No. EP 2482822 (Appln. No. 10821232.5), filed by Dr. Falk Pharma GmbH on Mar. 1, 2019; EPO's Decision revoking European Patent No. 2482822, dated Aug. 25, 2021, 23 pages.
Prosecution history excerpts from U.S. Appl. No. 12/896,005, filed Oct. 1, 2010, for Orally Administered Corticosteroid Compositions; Inventors Perrett, Stephen et al., issued as U.S. Pat. No. 8,771,729, 119 pages.
Prosecution history excerpts from U.S. Appl. No. 15/816,154, filed Nov. 17, 2017, for Orally Administered Corticosteroid Compositions; Inventors Perrett, Stephen et al., issued as U.S. Pat. No. 10,632,069, 90 pages.
Prosecution history excerpts from U.S. Appl. No. 17/236,295, filed Apr. 21, 2021, for Orally Administered Corticosteroid Compositions; Inventors Perrett, Stephen et al., issued as U.S. Pat. No. 11,266,598, 65 pages.
Shukla et al., "Mouth Dissolving Tablets I: An overview of formulation technology," Scientia Pharmaceutica (Mar. 6, 2009); 77(2): 309-326.
Siewert et al., "Eosinophilic gastroenteritis with severe protein-losing enteropathy: Successful treatment with budesonide," Digestive and Liver Disease Jan. 2006; 38(1): 55-59. Epub Dec. 1, 2005.
Svoboda et al., "Oral formulations of budesonide: a novel treatment for inflammatory bowel disease," Drugs of Today (Barc). Nov. 2008; 44(11): 857-863.
Tan et al., "Eosinophilic gastroenteritis treated with non-enteric-coated budesonide tablets," European Journal of Gastroenterology & Hepatology Apr. 2001; 13(4): 425-427.
The United States Pharmacopeia, "701 Disintegration", USP 32 (2009); NF 27, vol. 1, pp. 262-263, 4 pages.
Inter Partes Review Proceedings No. IPR2024-01197 filed Jul. 22, 2024, *Dr. Falk Pharma GMBH* (Petitioner) vs. *Ellodi Pharmaceuticals LP* (Patent Owner), U.S. Pat. No. 8,771,729 (U.S. Appl. No. 12/896,005), Decision Granting Institution of Inter Partes Review 35 U.S.C. § 314 dated Jan. 27, 2025, 43 pages.
Inter Partes Review Proceedings No. IPR2025-00052 filed Oct. 24, 2024, *Dr. Falk Pharma GMBH* (Petitioner) vs. *Ellodi Pharmaceuticals L.P.* (Patent Owner), U.S. Pat. No. 10,632,069 (U.S. Appl. No. 15/816,154), Petitioner's Supplemental Mandatory Notice: Related Matters Section dated and filed Dec. 17, 2024, 3 pages.
Inter Partes Review Proceedings No. IPR2025-00054 filed Oct. 24, 2024, *Dr. Falk Pharma GMBH* (Petitioner) vs. *Ellodi Pharmaceuticals L.P.* (Patent Owner), U.S. Pat. No. 11,246,828 (U.S. Appl. No. 16/821,464), Petitioner's Supplemental Mandatory Notice: Related Matters Section dated and filed Dec. 17, 2024, 3 pages.
Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), Petitioner's Supplemental Mandatory Notice: Related Matters Section dated and filed Dec. 17, 2024, 3 pages.
Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), U.S. Pat. No. 11,260,061 (U.S. Appl. No. 17/211,119), Petitioner's Supplemental Mandatory Notice: Related Matters Section dated and filed Dec. 17, 2024, 3 pages.
Allen, L.V. and LUNER, P. E., "Magnesium Stearate", Date of Revision: Aug. 9, 2005, In: Handbook of Pharmaceutical Excipients, 5th Ed. (2006), Raymond C. Rowe, et al. (eds); pp. 430-433, 7 pages.
Armstrong, N.A., "Mannitol", Date of Revision: Aug. 16, 2005, In: Handbook of Pharmaceutical Excipients, 5th Ed. (2006), Raymond C. Rowe, et al. (eds); pp. 449-453, 7 pages.

(56) References Cited

OTHER PUBLICATIONS

Conway, B.R., "Solid Dosage Forms", In: Pharmaceutical Manufacturing Handbook: Production and Processes (2008); by GAD, Shayne Cox; Ch. 4.1, pp. 235-265, 36 pages.
Declaration of Alan F. Parr, Pharm.D., Ph.D., in Support of Petition for Inter Partes Review (IPR2025-00052) of U.S. Pat. No. 10,632,069 dated Oct. 8, 2024, filed Oct. 24, 2024, 165 pages.
Declaration of Alan F. Parr, Pharm.D., Ph.D., in Support of Petition for Inter Partes Review (IPR2025-00054) of U.S. Pat. No. 11,246,828 dated Oct. 8, 2024, filed Oct. 24, 2024, 197 pages.
Declaration of Alan F. Parr, Pharm.D., Ph.D., in Support of Petition for Inter Partes Review (IPR2025-00055) of U.S. Pat. No. 9,486,407 dated Oct. 22, 2024, filed Oct. 24, 2024, 220 pages.
Declaration of Alan F. Parr, Pharm.D., Ph.D., in Support of Petition for Inter Partes Review (IPR2025-00056) of U.S. Pat. No. 11,260,061 dated Oct. 21, 2024, filed Oct. 24, 2024, 195 pages.
Definition of "Adsorption", McGraw-Hill Dictionary of Scientific and Technical Terms, Sixth Edition (2003); p. 41, 3 pages.
El-Arini, S.K., et al., "Evaluation of disintegration testing of different fast dissolving tablets using the texture analyzer", Pharm Dev Technol. 2002; 7(3): 361-371.
Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Patent Owner's Preliminary Response, dated and filed Oct. 29, 2024, 59 pages.
Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Patent Owner's Surreply, dated and filed Dec. 4, 2024, 8 pages.
Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Petitioner's Reply to Patent Owner's Preliminary Response dated and filed Nov. 26, 2024, 8 pages.
Inter Partes Review Proceedings No. IPR2024-01197 filed Jul. 22, 2024, Dr. Falk Pharma GMBH (Petitioner) vs. Ellodi Pharmaceuticals LP (Patent Owner), U.S. Pat. No. 8,771,729 (U.S. Appl. No. 12/896,005), Petitioner's Supplemental Mandatory Notice: Related Matters Section dated and filed Nov. 26, 2024, 4 pages.
Inter Partes Review Proceedings No. IPR2025-00052 filed Oct. 24, 2024, Dr. Falk Pharma GMBH (Petitioner) vs. Ellodi Pharmaceuticals L.P. (Patent Owner), Petition for Inter Partes Review of U.S. Pat. No. 10,632,069 (U.S. Appl. No. 15/816,154), dated and filed Oct. 24, 2024, and Petitioner Power of Attorney dated Jun. 8, 2024, 83 pages.
Inter Partes Review Proceedings No. IPR2025-00054 filed Oct. 24, 2024, Dr. Falk Pharma GMBH (Petitioner) vs. Ellodi Pharmaceuticals L.P. (Patent Owner), Petition for Inter Partes Review of U.S. Pat. No. 11,246,828 (U.S. Appl. No. 16/821,464), dated and filed Oct. 24, 2024, and Petitioner Power of Attorney dated Jun. 8, 2024, 91 pages.
Inter Partes Review Proceedings No. IPR2025-00055 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 9,486,407 (U.S. Appl. No. 14/294,660), dated and filed Oct. 24, 2024, and Petitioner Power of Attorney dated Jun. 8, 2024, 103 pages.
Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), Petition for Inter Partes Review of U.S. Pat. No. 11,260,061 (U.S. Appl. No. 17/211,119), dated and filed Oct. 24, 2024, and Petitioner Power of Attorney dated Jun. 8, 2024, 107 pages.
Inter Partes Review Proceedings No. IPR2025-00056 filed Oct. 24, 2024, *Dr. Falk Pharma GMBH* (Petitioner) vs. *Ellodi Pharmaceuticals L.P.* (Patent Owner), Redline comparison of Dohil (US2007/0111978) and Dohil 2009 (US2009/0191275), Exhibit 1059 filed Oct. 24, 2024, 47 pages.
Khan et al., "An Approach for Rapid Disintegrating Tablet: a Review", IJPRD, May 2011; vol. 3(3): 21; pp. 170-183.
Kibbe, A.H., "Povidone", Date of Revision: Aug. 30, 2005, In: Handbook of Pharmaceutical Excipients, 5th Ed. (2006), Raymond C. Rowe, et al. (eds); pp. 611-616, 9 pages.
Martin, Alfred, et al., "Adsorption at Solid Interfaces", (with the participation of Pilar Bustamente), In: Physical Pharmacy: Physical Chemical Principles in the Pharmaceutical Sciences, Fourth Edition (1993); Print. No. 10, Ch. 14, pp. 379-386, 11 pages.
Moreton, R.C., "Cellulose, Silicified Microcrystalline", Date of Revision: Aug. 26, 2005, In: Handbook of Pharmaceutical Excipients, 5th Ed. (2006), Raymond C. Rowe, et al. (eds); pp. 139-141, 5 pages.
Opposition Proceedings in European Patent No. EP 3041476 (Appln. No. 14842811.3), filed by Dr. Falk Pharma GmbH on Jul. 22, 2020; Interlocutory Decision dated Jan. 26, 2022, 30 pages.
Price, J.C., "Polyethylene Glycol", Date of Revision: Aug. 29, 2005, In: Handbook of Pharmaceutical Excipients, 5th Ed. (2006), Raymond C. Rowe, et al. (eds); pp. 545-550, 8 pages.
Prosecution history excerpts from U.S. Appl. No. 14/917,125, filed Sep. 5, 2014, for Corticosteroid Containing Orally Disintegrating Tablet Compositions for Eosinophilic Esophagitis; Inventors Gosselin, Michael A., issued as U.S. Pat. No. 10,471,071, 123 pages.
Prosecution history excerpts from U.S. Appl. No. 17/211,119, filed Mar. 24, 2021, for Corticosteroid Containing Orally Disintegrating Tablet Compositions for Eosinophilic Esophagitis; Inventors Gosselin, Michael A., issued as U.S. Pat. No. 11,260,061, 248 pages.
Prosecution history from U.S. Appl. No. 15/816,154 ('069 Patent) filed Nov. 17, 2017, for Orally Administered Corticosteroid Compositions; Inventors Perrett, Stephen et al., issued as U.S. Pat. No. 10,632,069, 408 pages.
Prosecution history from U.S. Appl. No. 16/821,464 ('828 Patent) filed Mar. 17, 2020, for Orally Administered Corticosteroid Compositions; Inventors Perrett, Stephen et al., issued as U.S. Pat. No. 11,246,828, 369 pages.
Roeder et al., "Safety and Efficacy of Fluticasone Propionate in the Topical Treatment of Skin Diseases", Skin Pharmacol Physiol (2005); 18 (1): 3-11.
The United States Pharmacopeial Convention, "701 Disintegration", Revision Bulletin, Official Aug. 1, 2008, USP 32 (2009); 3 pages.
U.S. Appl. No. 18/244,500, inventor Meltzer, Brian A., et al., filed Sep. 11, 2023.
U.S. Appl. No. 18/755,113, inventor Meltzer; Brian A, filed Jun. 26, 2024.
Wood, A.W., "Sucralose", Date of Revision: Aug. 17, 2005, In: Handbook of Pharmaceutical Excipients, 5th Ed. (2006), Raymond C. Rowe, et al. (eds); pp. 742-749, 11 pages.

ORALLY ADMINISTERED CORTICOSTEROID COMPOSITIONS

CROSS-REFERENCE TO RELATED APPLICATIONS

The present application is a continuation application of U.S. patent application Ser. No. 16/821,464, filed Mar. 17, 2020, which is a continuation application of U.S. patent application Ser. No. 15/816,154, filed Nov. 17, 2017 (U.S. Pat. No. 10,632,069, issued Apr. 28, 2020), which is a continuation of U.S. patent application Ser. No. 15/205,390, filed Jul. 8, 2016 (U.S. Pat. No. 9,849,084, issued Dec. 26, 2017), which is a continuation application of U.S. patent application Ser. No. 14/311,732, filed Jun. 23, 2014 (U.S. Pat. No. 9,387,167, issued Jul. 12, 2016), which is a divisional application of U.S. patent application Ser. No. 12/896,005, filed Oct. 1, 2010 (U.S. Pat. No. 8,771,729, issued Jul. 8, 2014), and claims the benefit of priority to U.S. Provisional Patent Application No. 61/247,642, filed Oct. 1, 2009, the disclosures of each of which are herein incorporated by reference in its entirety for all purposes.

TECHNICAL FIELD OF THE INVENTIONS

This invention relates to orally administered corticosteroid compositions, useful for the treatment of conditions associated with inflammation of the gastrointestinal tract.

BACKGROUND OF THE INVENTION

There are currently no approved topically administered anti-inflammatory medications for the treatment of conditions associated with inflammation of the upper portion of the gastrointestinal tract. One such condition, eosinophilic esophagitis (EE), is an inflammatory condition of the esophagus. It is characterized histologically by a proliferation of eosinophils. The disease is painful, leads to difficulty swallowing and predisposes patients to food impaction and other complications.

Experimental and "off-label" treatments for EE include directing steroid medications formulated and approved for inhalation to the back of the throat such that they are not appreciably inhaled, and instructing the patient to rinse their mouth immediately after administration and not to swallow food or water for two hours after administration. Rinsing is recommended because residual drug in the mouth and throat can lead to candiasis infection, and swallowing is contraindicated because it may wash drug away from the esophagus. Aqueous corticosteroid preparations intended for oral inhalation through nebulization are also mixed with sugars to produce a thickened and sweetened liquid for administration.

Off-label treatments for EE also include administration of corticosteroid tablets containing steroids such as prednisolone. However, systemic administration of corticosteroids is associated with a number of known and undesirable side-effects. For example, oral prednisolone can produce generalized suppression of immune function, and in children, particularly troubling side-effects from long term systemic exposure include growth retardation, which may lead to a reduction in adult height.

There is therefore a need in the art for orally administered corticosteroid formulations which provide topical (rather than systemic) treatment of inflammation of the gastrointestinal tract, particularly inflammation of the upper gastrointestinal tract, such as EE.

SUMMARY OF THE INVENTION

In one embodiment, the present invention is directed to a solid pharmaceutical composition comprising less than or equal to 20 mg of a corticosteroid, wherein the composition has no significant systemic glucocorticoid or mineralcorticoid activity after oral administration, wherein the solid pharmaceutical composition disintegrates within 60 seconds in simulated saliva when tested using the USP <701> Disintegration Test, and/or which disintegrates within 60 seconds when placed in the oral cavity of a human.

In another embodiment, the present invention is directed to a liquid pharmaceutical composition comprising a corticosteroid, and a pharmaceutically acceptable substantially non-aqueous liquid.

In another embodiment, the present invention is directed to a method for treating an inflammatory condition of the gastrointestinal tract. The method comprises administering to an individual in need thereof a pharmaceutical composition of the present invention.

In yet another embodiment, the present invention is directed to a liquid pharmaceutical composition comprising a corticosteroid, a pharmaceutically acceptable aqueous or substantially non-aqueous liquid, and a pharmaceutically acceptable phase change agent dissolved or suspended in the liquid, wherein after administration to a patient, the composition undergoes a change in physical properties upon contact with the gastrointestinal tract of the patient.

In yet another embodiment, the present invention is direction to a composition in solid or liquid form additionally comprising cyclodextrins.

The compositions of the present invention are useful for various conditions including the treatment of inflammatory conditions of the gastrointestinal tract. Accordingly, the present invention also provides a method for treating inflammatory conditions of the gastrointestinal tract in an individual. The method comprises administering to an individual in need thereof a pharmaceutical composition of the present invention.

DETAILED DESCRIPTION OF THE INVENTION

All documents (e.g., patents, patent publication, journal articles, etc.) cited in the present application are incorporated by reference in their entirety for all purposes.

The term "drug", "active" or "active pharmaceutical ingredient" as used herein includes a pharmaceutically acceptable and therapeutically effective compound (e.g., corticosteroid), pharmaceutically acceptable salts, stereoisomers and mixtures of stereoisomers, solvates (including hydrates), and/or esters thereof (e.g., of corticosteroid).

The terms "orally disintegrating tablet", "orally dispersing tablet", or "ODT" refer to a solid dosage form of the present invention, which disintegrates rapidly in the oral cavity of a patient after administration, without chewing. The rate of oral disintegration can vary, but is significantly faster than the rate of oral disintegration of conventional solid dosage forms or chewable solid dosage forms (i.e., tablets or capsules) which are intended to be swallowed immediately after administration. ODT compositions of the present invention can contain pharmaceutically acceptable ingredients which swell, dissolve or otherwise facilitating the disintegration or dissolution of the ODT composition. Such ingredients can include pharmaceutical a disintegrant, a sugar alcohol, a saccharide, or a mixture thereof, a water-soluble binder, a meltable solid (e.g., a wax), which can release the corticosteroid upon entering the stomach, etc.

The term "about", as used herein to refer to a numerical quantity, includes "exactly". For example, "about 60 seconds" includes 60 seconds, exactly, as well as values close to 60 seconds (e.g., 50 seconds, 55 seconds, 59 seconds, 61 seconds, 65 seconds, 70 seconds, etc.). When the term "about" is used in reference to a range of values, the term "about" refers to both the minimum and maximum value of the range (e.g., "about 1-50 µm" means "about 1 µm to about 50 µm").

The term "adhesive agent", as used herein refers to agents which promote adhesion of the corticosteroid to biological surfaces, and includes, but is not limited to bio-adhesive agents. Adhesive agents can include compounds which adhere to the oropharyngeal mucosa, as well as compounds which increase the residence time of the compositions of the present invention on the oropharyngeal mucosa of a patient.

The term "intimately associated", as used herein to describe the spatial relationship between two or more components of a composition refers to components that are intimately mixed, such as for example in mixtures, coatings and matrices.

The term "having no significant systemic glucocorticoid or mineralocorticoid activity", as used herein refers to corticosteroid compositions which do not provide a generalized effect in the body through absorption into the circulation, but do provide local effects through topical contact with a diseased tissue. Corticosteroids which have high systemic glucocorticoid potencies when administered orally include e.g., hydrocortisone, prednisone, prednisolone, methylprednisolone, dexamethasone, betamethasone, etc.) or mineralocorticoid potencies (e.g., alsosterone). These corticosteroids may be suitable for use in the compositions of the present invention if they are used at a sufficiently low dose, or are otherwise formulated such that they do not have significant systemic glucocorticoid or mineralcorticoid activity. Exemplary corticosteroids suitable for use in the compositions of the present invention include, but are not limited to budesonide, fluticasone, flunisolide, ciclesonide, mometasone, beclomethasone and tixocortol.

The term "bio-gelling polymer" as used herein refers to a polymer forms a gel under GI tract physiological conditions, for example, upon contact with physiological fluids or at physiological temperature.

The term "substantially non-aqueous liquid" refers to liquids which are completely anhydrous, or include only small amounts of water (e.g. less than about 10% water, for example less than about 9%, less than about 8%, less than about 7%, less than about 6%, less than about 5%, less than about 4%, less than about 3%, less than about 2%, or less than about 1% water).

The term "phase change agent" refers to an agent which, upon dissolution or suspension in the substantially non-aqueous liquids of the present invention, causes the liquid pharmaceutical compositions of the present invention to undergo a change in physical properties after administration to a patient. For example, such changes in physical properties include precipitation of the dissolved or suspended components of the composition (e.g. the corticosteroid, optional excipients, and the phase change agent); gelation of the composition (e.g., formation of a hydrogel of the phase change agent and optionally excipients, wherein the hydrogel comprises at least a portion of the corticosteroid); or an increase in viscosity of the composition. These changes in physical properties have the effect of increasing or enhancing contact of the corticosteroid to the mucosa of the gastrointestinal tract of the patient.

Unless indicated otherwise, all percentages and ratios are calculated by weight. Unless indicated otherwise, all percentages and ratios are calculated based on the total composition.

The solid and liquid pharmaceutical compositions of the present invention are suitable for topical administration of a corticosteroid to the gastrointestinal tract, for example the upper gastrointestinal tract such as the esophagus. Topical administration of a corticosteroid for conditions associated with inflammation of the gastrointestinal tract is desirable because it results in fewer side-effects than systemic corticosteroid administration. Such side-effects are reduced still further with the use of corticosteroids which do not have significant systemic glucocorticoid or mineralocorticoid activity because of their reduced systemic exposure.

The pharmaceutical compositions of the present invention are suitable for treating inflammatory conditions of the gastrointestinal tract, for example inflammatory conditions of the upper gastrointestinal tract such as the esophagus. Thus, the present invention includes treating inflammatory conditions of the gastrointestinal tract by administering to a patient in need thereof a solid or liquid pharmaceutical composition of the present invention. Inflammatory conditions of the gastrointestinal tract which may be treated according to the present invention include inflammation of the esophagus, inflammation of the glottis, inflammation of the epiglottis, inflammation of the tonsils, inflammation of the oropharynx, eosinophilic esophagitis, gastroesophageal reflux disease (GERD), non-erosive reflux disease (NERD), erosive esophagitis, Barrett's esophagus, eosinophilic gastroenteritis, hypereosinophilic syndrome, corrosive (caustic) chemical esophagitis, radiation-induced esophagitis, chemotherapy-induced esophagitis, transient drug-induced esophagitis (also known as medication esophagitis), persistent drug-induced esophagitis, Crohn's disease of the esophagus, scleroderma, and scleroderma sine scleroderma, systemic lupus erythematosus, systemic vasculitides, leukocytoclastic vasculitis, polyarteritis nodosa, Churg-Strauss syndrome, rheumatoid vasculitis, and pseudomembranous esophagitis.

In other embodiments, the pharmaceutical compositions of the present invention are suitable for treating inflammatory conditions of the gastrointestinal tract such as an autoimmune disease, Behcet's syndrome, Kawasaki disease, X-linked lymphoproliferative syndrome; an infectious viral disease caused by one or more of the following viruses: Adenoviridae, Coronaviridae, Coxsackie virus, Herpes simplex, HIV, Influenza (Type A), Lassa virus, Epstein-Barr virus, Parainfluenza, or Respiratory syncytial virus; an infectious bacterial disease caused by one or more of the following bacteria: *Arcanobacterium hemolyticum, Chlamydia (Chlamydophila), Corynebacterium, Francisella tularensis,* Group A, C, G *Streptococcus, S. pneumoniae, S. pyogenes, Haemophilus* influenza type B, *Mycoplasma* pneumonia, *Neisseria* gonorrhea, Multiple (e.g. peritonsillar cellulitis/abscess); an infectious fungal disease caused by *Candida* (e.g. *Candida albicans*) or *Histoplasma* (e.g. *H capsulatum*); inflammation caused by injury or an irritant selected from the group consisting of an airway foreign body, chloroacetophenone, chlorobenzylidene malononitrile, chronic smoke exposure, morpholine, sulfuryl fluoride, and scalded throat; lepidopterism, Seasonal allergic pharyngitis, and Stevens-Johnson syndrome; or periodic fever; etc.

In one embodiment, the present invention includes a method for treating inflammation of the esophagus comprising administering to a patient in need thereof a pharmaceutical composition of the present invention. In one such embodiment, the present invention includes a method for treating eosinophilic esophagitis comprising administering to a patient in need thereof a pharmaceutical composition of the present invention.

In another embodiment, the present invention includes a method for treating gastroesophageal reflux disease (GERD), nonerosive reflux disease (NERD) or erosive esophagitis comprising administering to an individual in need thereof a pharmaceutical composition of the present invention.

In another embodiment, the present invention includes a method for treating a food allergy with an identified allergen, e.g., "atopic IBS", and "atopic bowel".

In one embodiment, the present invention provides a solid pharmaceutical composition which comprises less than or equal to 20 mg of a corticosteroid, wherein the composition has no significant systemic glucocorticoid or mineralocorticoid activity, and wherein the solid pharmaceutical composition disintegrates within 60 seconds in simulated saliva when tested using the USP <701> Disintegration Test. In another embodiment, the solid pharmaceutical compositions of the present invention disintegrate within 60 seconds in the oral cavity of the patient, e.g. human. In still other embodiments, the solid pharmaceutical compositions of the present invention disintegrate within 30 seconds in simulated saliva (using the USP <701> Disintegration Test), or in the oral cavity of a patient. In still other embodiments, the solid or liquid pharmaceutical compositions of the present invention topically provide a therapeutically effective amount of a corticosteroid to inflamed tissues of the gastrointestinal tract, after oral administration to a patient in need thereof.

Solid pharmaceutical compositions of the present invention can include, for example, an ODT (as described herein), a wafer, a film, or other solid dosage form which disintegrates or dissolves rapidly in the mouth to form a solution or dispersion of a corticosteroid, which can readily be swallowed.

In another embodiment, the present invention provides a liquid pharmaceutical composition comprising a corticosteroid and a pharmaceutically acceptable solvent, wherein the liquid pharmaceutical composition has no significant systemic glucocorticoid or mineralocorticoid activity. In one such embodiment the composition also includes a pharmaceutically acceptable bio-gelling polymer dissolved in the solvent, and the composition increases in viscosity upon contact with the gastrointestinal tract of an individual. In other embodiments, the liquid compositions of the present invention comprise a corticosteroid complex with a cyclodextrin, typically suspended or dissolved in a liquid carrier. The liquid compositions of the present invention may be in the form of a solution or a suspension. Liquid pharmaceutical compositions according to the present invention are compositions which are liquids at standard temperature and pressure conditions.

Suitable pharmaceutically acceptable liquids which may be used in the liquid pharmaceutical compositions of the present invention include, for example, alcohols, oils, glycols, glycol ethers, pyrrolidones, polyethylene glycols, N-methyl-2-pyrrolidone (NMP), 2-pyrrolidone, glycerol, tetraglycol, glycerol formal, solketal, ethyl acetate, ethyl lactate, ethyl butyrate, dibutyl malonate, tributyl citrate, tri-n-hexyl acetylcitrate, diethyl succinate, diethyl glutarate, diethyl malonate, triethyl citrate, triacetin, tributyrin, diethyl carbonate, propylene carbonate, acetone, methyl ethyl ketone, dimethyl sulfoxide, dimethyl sulfone, tetrahydrofuran, caprolactam, N,N-di ethyl-m-toluamide, 1-dodecylazacycloheptan-2-one, 1,3-dimethyl-3,4,5,6-tetrahydro-2 (1H)-pyrimidinone, and combinations thereof. In one embodiment, the liquid is selected from the group of alcohols, oils, glycols, glycol ethers, pyrrolidones, polyethylene glycols, glycerol and combinations thereof. In one such embodiment, the liquid is selected from the group of ethanol, glycerol, propylene glycol, glycerides, polyethylene glycol with a molecular weight between about 200 and 600, and combinations thereof. In other embodiments, the liquid pharmaceutical compositions of the present invention can comprise aqueous suspensions or solutions of a corticosteroid.

In one embodiment the bio-gelling polymer is a thermosensitive polymer. Suitable thermosensitive polymers include polyacrylamides, such as poly(N-isopropylacrylamide), as well as poly(ether-ester) copolymers, such as poly (ethylene glycol-(DL-lactic acid-co-glycolic acid)-ethylene glycol). Such thermosensitive polymers can precipitate or cause an increase in viscosity of the liquid compositions of the present invention upon administration to a patient, and subsequent warming in the gastrointestinal tract. Thus, the compositions of the invention precipitate on or have a longer residence time on the gastrointestinal mucosa the patient, thereby increasing the topical contact of the corticosteroid on the gastrointestinal mucosa. Consequently, the contact of the corticosteroid with the gastrointestinal mucosa is enhanced and/or prolonged.

In another embodiment, the compositions of the present invention include a bioadhesive agent, which is a lipid or a mixture of lipids. Such lipids or lipid mixtures may undergo a phase transition on contact with wetted biological surfaces to form an adhesive film. Examples of such lipids include mixtures of so-called membrane and non-membrane lipids which will typically form lamellar and non-lamellar structures, such as hexagonal or cubic phases, respectively. Examples of such lipids are glycerphospholipids such as phosphatidyl choline, and diacyl glycerols such as glycerol dioleate. Such self-organizing structures demonstrate superior spreading and adhesion to biological surfaces and have the advantage or being pharmaceutically acceptable materials. Advantageously the active agent, e.g. a corticosteroid may be dissolved in the lipid component.

Suitable non-aqueous solvents which may be included in the liquid pharmaceutical compositions of the present invention include pharmaceutically acceptable non-aqueous solvents in which the particular bio-gelling polymer is soluble. For example, the solvent may be an alcohol (e.g., ethanol), N-methyl-pyrrolidone (NMP), glycerol, propylene glycol, liquid polyethylene glycol, diethylene glycol monoethyl ether and mixtures thereof. In certain embodiments the solvent is water-miscible and the bio-gelling polymer is water-insoluble, so that upon administration the solvent mixes rapidly with the water from the digestive tract of the patient, causing the bio-gelling polymer and corticosteroid to precipitate on the gastrointestinal mucosa of the patient. Consequently, the contact of the corticosteroid with the gastrointestinal mucosa is enhanced and/or prolonged.

Other bio-gelling polymers which may be included within the liquid pharmaceutical compositions of the present invention include cellulose derivatives (e.g., esters and/or ethers, crosslinked cellulose esters and/or ethers) cellulose esters, methacrylic acid and methacrylate polymers, polylactides, polyglycolides, polycaprolactones, polydioxannones, polycarbonates, polyhydroxybutyrates, polyalkyene oxalates, polyanhydrides, polyamides, polyesteramides, polyurethanes, polyacetals, polyketals, polyorthocarbonates, polyphosphazenes, polyhydroxyvalerates, polyalkylene succinates, poly(malic acid), poly(amino acids), chitin, chitosan, polyorthoesters, and copolymers, terpolymers and mixtures thereof. Bio-gelling polymers swell, and/or form hydrogels upon contact with moisture in the gastrointestinal tract, thereby adhering or increasing the viscosity of the compositions of the present invention on the mucosa of the gastrointestinal tract. Consequently, the contact of the corticosteroid with the gastrointestinal mucosa is enhanced and/or prolonged.

In certain embodiments, the liquid pharmaceutical compositions of the present invention increase in viscosity upon contact with the gastrointestinal tract of an individual. In one embodiment, the increase in viscosity is at least 50% (relative to the viscosity prior to administration). In another such embodiment, the increase in viscosity is at least 100%. In yet another such embodiment, the increase in viscosity is at least 200%. The viscosity of the compositions before contact with the gastrointestinal tract of an individual may be measured using a viscometer. The change in viscosity of the compositions upon contact with the gastrointestinal tract of an individual may be determined by measuring the viscosity of the composition under simulated physiological conditions. For example, the viscosity of a given composition may be measured in simulated saliva.

Suitable corticosteroids which may be included in the pharmaceutical compositions of the present invention include budesonide, fluticasone, flunisolide, ciclesonide, mometasone, beclomethasone, tixocortol and salts, solvates, and esters thereof. In a particular embodiment, the compositions of the present invention comprise fluticasone. In other embodiments, the compositions of the present invention comprise budesonide. Corticosteroids which typically have systemic glucocorticoid or mineralocorticoid activity when administered orally can also be used in the compositions of the present invention, if the composition is modified to reduce or suppress systemic uptake of the corticosteroid.

The amount of corticosteroid present in the pharmaceutical compositions of the present invention will depend upon the particular corticosteroid utilized. In general, however, the amount will be selected so as to maximize the therapeutic benefit from topical administration while minimizing systemic absorption. In the case of solid pharmaceutical compositions of the present invention, the amount of corticosteroid in the composition typically is less than or equal to 20 mg. In one embodiment the amount of corticosteroid in the pharmaceutical composition is between about 0.01 mg and about 20 mg. In another embodiment the amount of corticosteroid in the pharmaceutical composition is between about 1 mg and about 15 mg. In still another embodiment the amount of corticosteroid in the pharmaceutical composition is between about 2 mg and about 10 mg. In yet another embodiment the amount of corticosteroid in the pharmaceutical composition is between about 2 mg and about 5 mg. In still other embodiments, the amount of corticosteroid is about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 90 mg, or about 20 mg, inclusive of all ranges and subranges therebetween.

Typical amounts of corticosteroid in the solid pharmaceutical compositions of the present invention include about 0.25 mg, about 0.5 mg, about 1 mg, about 1.5 mg, about 2 mg, about 2.5 mg, about 3 mg, about 3.5 mg, about 4 mg, about 4.5 mg and about 5 mg. In the case of liquid pharmaceutical compositions of the present invention, the concentration of corticosteroid in the composition typically is such that an amount of corticosteroid consistent with the amounts described above (i.e., 0.01 mg to 20 mg) may be conveniently administered to an individual. For example, the concentration of corticosteroid may be such that a single pump from a spray pump device delivers about 0.05 mg, or any other therapeutically effective pre-selected amount, of corticosteroid to the oral cavity of an individual. In a particular embodiment, the compositions of the present invention comprise about 0.25 mg of fluticasone.

Upon administration of a solid pharmaceutical composition of the present invention to an individual, the composition disintegrates in the patient's oral cavity. In one embodiment, the composition of the present invention is in the form of an ODT. An ODT comprises drug containing particles (e.g., a corticosteroid as described herein optionally coated or combined with an adhesive agent as described herein), combined with rapidly dispersing microgranules. Rapidly dispersing microgranules can be prepared as described in US 2005/0232988 or US 20010014340 by granulating a disintegrant having an average particle size of not more than about 30 µm with a sugar alcohol and/or saccharide having an average particle size of not more than about 30 µm. The granulation can be carried out, for example, in a high shear granulator with approximately 20-25% water as the granulating fluid, and if needed wet milled and dried to produce rapidly dispersing microgranules having an average particle size of not more than about 300 µm (e.g., about 175-300 µm).

The ratio of the disintegrant to the sugar alcohol, saccharide, or mixture thereof in the rapidly dispersing microgranules ranges from about 90/10 to about 99/01, for example about 90/10, about 91/9, about 92/8, about 93/7, about 94/6, about 95/5, about 96/4, about 97/3, about 98/2, about 99/1, inclusive of all values, ranges, and subranges therebetween.

The ratio of the rapidly dispersing microgranules to drug-containing particles ranges from about 5/1 to about 1/1, including about 5/1, 4/1, 3/1, 2/1, 1/1, inclusive of all values, ranges, and subranges therebetween.

The corticosteroid containing particles of the ODT dosage form should also have a small enough particle size such that after disintegration of the ODT in the oral cavity of the patient, a smooth, easy-to-swallow suspension results. In most embodiments in which the pharmaceutical compositions of the present invention is provided as an ODT dosage form, the average particle size of the taste-masked non-opioid analgesic/opioid analgesic drug-containing microparticles is not more than about 400 µm, or in some embodiments not more than about 300 µm.

The ODT dosage form as described herein may also include pharmaceutically acceptable excipients typically used in disintegrating tablet formulations such as microcrystalline cellulose and spray dried mannitol (compressible diluents), croscarmellose sodium or crospovidone (super disintegrant), coloring agents, and optionally magnesium stearate or sodium stearyl fumarate (lubricant intragranularly mixed or used externally to lubricate die and punch surfaces).

Tablet dosage forms, including ODT dosage forms, comprising the pharmaceutical composition of the present invention have a low friability, e.g., less than about 1%, (e.g., less than about 0.9%, less than about 0.8%, less than about 0.7%, less than about 0.6%, less than about 0.5%, less than about 0.4%, less than about 0.3%, etc., inclusive of all ranges and subranges therebetween) in order to have sufficient durability to withstand handling, shipping, and/or packaging in push-through blister packaging.

A non-limiting list of suitable disintegrants for the rapidly dispersing microgranules includes crospovidone (cross-linked PVP), sodium starch glycolate, cross-linked sodium carboxymethylcellulose, calcium silicate, and low substituted hydroxypropyl cellulose. The amount of disintegrant in the ODT is typically in the range of about 1% to about 10% by weight.

A non-limiting list of suitable sugar alcohols includes mannitol, sorbitol, xylitol, maltitol, arabitol, ribitol, dulcitol, iditol, isomalt, lactitol, erythritol and combinations thereof. A non-limiting list of suitable saccharides includes lactose, sucrose, maltose, and combinations thereof. The amount of sugar alcohol and/or saccharide in the ODT ranges from about 30% to about 70% by weight.

Pharmaceutically acceptable excipients include fillers, diluents, glidants, disintegrants, binders and lubricants. Other pharmaceutically acceptable excipients include acidifying agents, alkalizing agents, preservatives, antioxidants, buffering agents, chelating agents, coloring agents, complexing agents, emulsifying and/or solubilizing agents, flavors, perfumes, humectants, sweetening agents and wetting agents.

Examples of suitable fillers, diluents and/or binders include lactose (e.g. spray-dried lactose, α-lactose, (β-lactose, TABLETOSE®, various grades of PHARMATOSE®, MICROTOSE® or FAST-FLO®), microcrystalline cellulose (various grades of AVICEL®, CEOLUS®, ELCEMA®, VIVACEL®, MING TAI® or SOLKA-FLOC®), hydroxypropylcellulose, L-hydroxypropylcellulose (low substituted), low molecular weight hydroxypropyl methylcellulose (HPMC) (e.g. Methocel E, F and K from Dow Chemical, Metolose SH from Shin-Etsu, Ltd), hydroxyethylcellulose, sodium carboxymethylcellulose, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate and collagen.

Examples of suitable diluents include e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose and sugar.

Examples of suitable disintegrants include e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, and carboxymethyl starch (e.g. PRIMOGEL® and EXPLOTAB®).

Specific examples of glidants and lubricants include stearic acid, magnesium stearate, calcium stearate or other metallic stearates, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate and sodium acetate.

Other excipients include e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents and agents for modified release.

Other functional excipients such as cyclodextrins may be used, for example as taste-masking agents (e.g., by means of their complexation with the corticosteroid). Cyclodextrins may also be used as a carrier and/or a dispersant to facilitate delivery and distribution of the corticosteroid at the intended site of therapeutic activity.

Compositions of the present invention in the form of an ODT disintegrate into corticosteroid containing particles while sugar alcohol/saccharide-containing granules included within the composition rapidly dissolve, thereby forming a smooth suspension that can be readily swallowed.

Other corticosteroid-containing orally disintegrating or orally dissolving dosage forms such as wafers or films can also be used. For example, wafers can include dried or lyophilized compositions such as orally disintegrating or dissolving dosage forms prepared using ZYDIS® lyophilization technology (e.g., as described in U.S. Pat. No. 6,316,027), containing a corticosteroid as the active pharmaceutical ingredient. Film dosage forms can include edible films such as those described in U.S. Pat. Nos. 6,596,298, 6,740,332, containing a corticosteroid as the active pharmaceutical ingredient.

The rate of disintegration of the compositions of the present invention in the oral cavity of an individual can be on the order of about 60 seconds or less, about 50 seconds or less, about 40 seconds or less, about 30 seconds or less, about 20 seconds or less, or about 10 seconds or less.

The rate of disintegration of the solid pharmaceutical compositions of the present invention can be measured using various in vitro test methods, for example the USP <701> Disintegration Test. When using the USP <701> Disintegration Test, the rate of disintegration of the compositions of the present invention typically is about 60 seconds or less, about 45 seconds or less, about 30 seconds or less, about 20 seconds or less, or about 10 seconds or less.

In other embodiments, the solid pharmaceutical compositions of the present invention can have any rate of disintegration or dissolution in the oral cavity of a patient which provides a therapeutically effective amount of corticosteroid to the inflamed tissues of the gastrointestinal tract. For example, in some embodiments, solid pharmaceutical compositions according to the present invention include compositions that provide about 0.5 mg to about 20 mg of the corticosteroid to the inflamed tissues of the gastrointestinal tract after oral administration.

In one embodiment, the solid pharmaceutical compositions of the present invention include an adhesive agent. Suitable adhesive agents include sucrose aluminum sulfate complex, chitosan and derivatives thereof (e.g., trimethylchitosan, chitosan salts), polyvinylpyrrolidone, methylcellulose, sodium carboxymethylcellulose, hydroxypropyl cellulose, cross-linked or uncross-linked polyacrylates, cross-linked polyacrylates, acidic cross-linked or uncross-linked polyacrylates, polyacrylic acid homopolymers or copolymers, aminoalkyl methacrylate copolymers, methacrylic acid/methylmethacrylate copolymer, alkylacrylate/alkylmethacrylate copolymers, ammoniomethacrylate copolymers, Eudragit® polymers (E, L, S, NE, RL, and RS grades), carbomer homopolymers or copolymers, hydrophilic polysaccharide gums, maltodextrins, cross-linked alginate gum gels, polycarboxylated vinyl polymers, pectins, xanthan gums, alginic acid, modified alginic acids, and combinations thereof.

In certain embodiments of the solid pharmaceutical compositions of the present invention, the corticosteroid and the adhesive agent are intimately associated. In one such embodiment the solid pharmaceutical composition comprises corticosteroid surrounded or encapsulated by the adhesive agent. In another such embodiment the solid pharmaceutical composition comprises corticosteroid disposed on the surface of the adhesive agent. In still other embodiments, the solid pharmaceutical composition comprises corticosteroid mixed or granulated with the adhesive agent.

Topical administration of a corticosteroid to the oral cavity of individuals has been associated with candidiasis infection. Consequently, in one embodiment pharmaceutical compositions of the present invention include an antifungal agent. Suitable antifungal agents include, but are not limited to mitotic inhibitor antifungals, pyrimidine analog antifungals, polyene antifungals, benzimidazole antifungals, imidazole antifungals, polyene antifungals, triazole antifungals, thiazole antifungals, allylamine antifungals, echinocandin antifungals, and other "uncategorized" antifungals recognized in the art that do not fall within any of the above categories (e.g., tolnaflate and ciclopirox). For example, suitable antifungal agents which may be included in the solid pharmaceutical compositions of the present invention include abafungin, amorolfine, anidulafungin, bifonazole, butenafine, butoconazole, candicin, caspofungin, ciclopirox, clotrimazole, econazole, fenticonazole, filipin, fluconazole, flucytosine, griseofulvin, isavuconizole, isoconazole, itraconazole, ketoconazole, micafungin, miconazole, miconazole nitrate, naftifine, natamycin, nystatin, oxiconazole, posaconazole, pramiconazole, ravuconazole, rimocidin, setaconizole, sulconazole, terbafine, terconazole, tioconazole, tolnaftate, undecylenic acid, and voriconazole.

In another embodiment, pharmaceutical compositions of the present invention include an antiviral agent. Antiviral agents which may be included in the solid pharmaceutical compositions of the present invention include interferons, nucleoside and nucleotide reverse transcriptase inhibitors, non-nucleoside reverse transcriptase inhibitors, protease inhibitors, integrase inhibitors, fusion inhibitors, maturation inhibitors, guanosine analogs, purine analogs, pyrimidine analogs, and other "uncategorized" antiviral drugs recognized in the art which do not fall within any of the above classes (e.g. foscarnet and miltefosine). For example, suitable antifungal agents which may be included in the solid pharmaceutical compositions of the present invention include abacavir, aciclovir (also known as acyclovir), adefovir, amantadine, amdoxovir, amprenavir, aplaviroc, apricitabine, arbidol, atazanavir, bevirimat, BMS-488043, boceprevir, brivudine, cidofovir, DCM205, docosanol, delavirdine, didanosine, durunavir, efavirenz, elvitegravir, elvucitabine, emtricitabine, enfuvirtide, epigallocatechin gallate, etravirine, famciclovir, fosamprenavir, ganciclocvir, globoidnan A, griffithsin, ibalizumab, idoxuridine, indinavir, lamivudine, lopinavir, loviride, maraviroc, nelfinavir, nevirapine, oseltamivir, pegylated interferon α-2a, pegylated interferon α-2b, penciclovir, peramivir, plerixafor, PRO 140, racivir, raltegrvir, ritonavir, ribavirin, rimantadine, rlipivirine, saquinavir, stampidine, stavudine, tenofovir, tipranavir, TNX-355, trifluridine, tromantadine, valaciclovir, valganciclovir, vicriviroc, vidarabione, viramidine, vivecon, zalcitabine, zanamivir, and zidovudine.

In one embodiment, the solid pharmaceutical compositions of the present invention comprise corticosteroid-containing granules. The corticosteroid-containing granules may be granules comprising corticosteroid crystals and a film-forming binder, e.g., prepared by granulation. The corticosteroid crystals can have an average particle size ranging from about 1-300 for example about 1-50 μm, about 1-100 μm, about 1-150 μm, about 1-200 μm, about 1-250 μm, about 50-100 μm, about 50-150 μm, about 50-200 about 50-250 μm, about 50-300 μm, about 100-150 μm, about 100-200 μm, about 150-200 μm, about 150-250 μm, about 150-300 μm, about 200-250 μm, about 200-300 μm, or about 250-300 μm.

In another embodiment, the corticosteroid may be in the form of crystals. Such crystals may have an average size in the sub-micron range (e.g., average particle size of about <1 μm), or may be nanoparticles (e.g., average particle size in the range of about 1-100 nm).

In yet another embodiment, the corticosteroid may be present in amorphous form, for example in association with a stabilizing agent which limits drug recrystallization, e.g., polyvinylpyrrolidone (PVP) (including homo- and copolymers of polyvinylpyrrolidone and homopolymers or copolymers of N-vinylpyrrolidone); crospovidone; gums; cellulose derivatives (including hydroxypropyl methylcellulose (HPMC), hydroxypropyl methylcellulose phthalate, hydroxypropyl cellulose, ethyl cellulose, hydroxyethylcellulose, sodium carboxymethyl cellulose, calcium carboxymethyl cellulose, sodium carboxymethyl cellulose, and others); dextran; acacia; homo- and copolymers of vinyllactam, and mixtures thereof, cyclodextrins; gelatins; hypromellose phthalate; sugars; polyhydric alcohols; polyethylene glycol (PEG); polyethylene oxides; polyoxyethylene derivatives; polyvinyl alcohol; propylene glycol derivatives and the like, sodium lauryl sulphate, TWEEN® surfactants, EUDRAGIT® polymers; and combinations thereof.

The film-forming binder may comprise any suitable binder used in granulation. Non-limiting examples of suitable film-forming binders include water-soluble, alcohol-soluble or acetone/water soluble binders, e.g. polyvinylpyrrolidone (PVP), corn starch, polyethylene oxide, polyethylene glycol, hydroxypropyl methylcellulose (HPMC), methylcellulose, or hydroxypropylcellulose (HPC). The amount of film-forming binder in the corticosteroid-containing granules can range from about 0.5% to about 10%, including about 0.5%-1%, about 0.5%-2%, about 0.5%-5%, about 0.5%-7%, about 1%-2%, about 1%-5%, about 1%-7%, about 1%-10%, about 2%-5%, about 2%-7%, about 2%-10%, about 5%-7%, about 5%-10%, and about 7%-10%.

The corticosteroid-containing granules of the present invention may also include other pharmaceutically acceptable ingredients, for example, fillers or diluents. Non-limiting examples of other pharmaceutically acceptable ingredients for the corticosteroid-containing granules include, for example, mannitol, lactose, microcrystalline cellulose, potassium sulfate, calcium phosphate, modified starch, and mixtures thereof. The amount of other pharmaceutically acceptable ingredients (e.g. fillers or diluents) in the corticosteroid-containing granules can range from about 5%-80%, including about 5%-70%, about 5%-60%, about 5%-50%, about 5%-40%, about 5%-30%, about 5%-20%, about 5%-15%, about 5%-10%, about 10%-70%, about 10%-60%, about 10%-50%, about 10%-40%, about 10%-30%, about 10%-20%, about 10%-15%, about 20%-70%, about 20%-60%, about 20%-50%, about 20%-40%, about 20%-30%, about 20%-25%, about 30%-70%, about 30%-60%, about 30%-50%, about 30%-40%, about 30%-35%, about 40%-70%, about 40%-60%, about 40%-50%, about 40%-45%, about 50%-70%, about 50%-60%, about 50%-55%, about 60%-70%, or about 60%-65%.

In another embodiment, the corticosteroid-containing granules of the present invention can be in the form of corticosteroid-layered beads. Corticosteroid-layered beads comprise a core, e.g. a pharmaceutically acceptable sugar bead, coated with a corticosteroid layer. Such corticosteroid-layered beads can be prepared, for example, by dissolving or suspending corticosteroid in a polymeric binder solution, which is then sprayed or coated onto inert particles (e.g., sugar spheres or cellulose spheres (CELPHERE®). Suitable polymeric binders include any of those disclosed herein, for example starches, modified celluloses (e.g., hydroxypropylcellulose, carboxymethylcellulose sodium), alginic acid, polyvinyl pyrrolidone (povidone), and mixtures thereof. The amount of corticosteroid in the corticosteroid layer, and the thickness of the corticosteroid layer can be modified to provide a therapeutically effective dose of corticosteroid. The corticosteroid-containing layer comprises about 90%-99% corticosteroid, and about 1% to about 10% binder.

The corticosteroid-containing granules of the present invention can be prepared by any suitable method. For example, the corticosteroid-containing granules can be prepared by granulation of corticosteroid crystals, one or more disintegrants, and one or more fillers (e.g., sugar alcohol, saccharide and/or microcrystalline cellulose) in a high shear granulator or a fluid-bed granulator using a solution of one or more polymeric binders, and dried in fluid bed equipment or on trays in a conventional oven to produce the corticosteroid-containing granules.

The solid pharmaceutical compositions of the present invention may include rapidly dispersing granules comprising a disintegrant and a sugar alcohol and/or a saccharide. The disintegrant-containing granules can include disintegrants or so-called super-disintegrants, e.g. crospovidone (crosslinked PVP), sodium starch glycolate, crosslinked sodium carboxymethyl cellulose, low substituted hydroxypropylcellulose, and mixtures thereof. The amount of disintegrant in the rapidly dispersing granules can range from about 1%-10%, or about 5%-10% of the total weight of the rapidly dispersing granules, including all ranges and subranges therebetween.

Sugar alcohols are hydrogenated forms of carbohydrates in which the carbonyl group (i.e., aldehyde or ketone) has been reduced to a primary or secondary hydroxyl group. Non-limiting examples of suitable sugar alcohols for the rapidly dispersing granules of the pharmaceutical compositions of the present invention include e.g. arabitol, isomalt, erythritol, glycerol, lactitol, mannitol, sorbitol, xylitol, maltitol, and mixtures thereof. The term "saccharide" is synonymous with the term "sugars" includes monosaccharides such as glucose, fructose, the lactose, and ribose; and disaccharides such as sucrose, lactose, maltose, trehalose, and cellobiose. In one embodiment, non-limiting examples of suitable saccharides for use in the compositions of the present invention include e.g. lactose, sucrose, maltose, and mixtures thereof. In another embodiment, the rapidly dispersing granules comprise at least one disintegrant in combination with a sugar alcohol. In another embodiment, the rapidly dispersing granules comprise at least one disintegrant in combination with a saccharide. In yet another embodiment, the disintegrant-containing granules comprise at least one disintegrant in combination with a sugar alcohol and a saccharide. The amount of sugar alcohol and/or saccharide in the rapidly dispersing granules ranges from about 99%-90%, or about 95%-90% of the total weight of the disintegrant-containing granules, including all ranges and subranges therebetween. In one embodiment, the average particle size of a sugar alcohol and/or saccharide is 30 μm or less, for example about 1-30 μm, about 5-30 μm, about 5-25 μm, about 5-20 μm, about 5-15 μm, about 5-10 μm, about 10-30 μm, about 10-25 μm, about 10-20 μm, about 10-15 μm, about 15-30 μm, about 15-25 μm, about 15-20 μm, about 20-30 μm, about 20-25 μm, or about 25-30 μm.

The corticosteroid-containing particles (e.g., crystals, granules, or drug-layered beads) of the solid pharmaceutical compositions of the present invention can also be coated with a taste-masking layer to improve the palatability of the composition. The corticosteroid-containing particles can be taste-masked by coating the corticosteroid-containing particles (e.g., crystals, granules, or drug-layered beads) with a water-insoluble polymer. Non-limiting examples of suitable water-insoluble polymers for the taste-masking layer include ethylcellulose, polyvinyl acetate (PVA), cellulose acetate (CA), cellulose acetate butyrate (CAB), methacrylate copolymers, such as those available under the tradename "EUDRAGIT" (e.g., type RL, RS, and NE30D), and combinations thereof.

In one embodiment, the water-insoluble polymer is ethylcellulose having a viscosity of about 90-110 cps when tested in an Ubbelohde viscometer as a 5 weight % 80:20 toluene/ethanol solution at 25° C.

In one embodiment, the solid pharmaceutical compositions of the present invention comprise about 25-35% of corticosteroid crystals, microencapsulated with a taste-masking layer comprising a water-insoluble polymer (e.g., ethylcellulose); about 60-70% of rapidly-dispersing granules (e.g., comprising crospovidone and mannitol); about 5% of additional disintegrant (e.g., crospovidone); about 1% of one or more flavors, and about 0.5%-1% of a sweetener (e.g., sucralose).

The method of producing drug-layered beads in one embodiment of the invention comprises dissolving or suspending corticosteroid in a polymeric binder solution and layering onto inert particles (50-100 mesh or 150-300 μm in diameter) such as sugar spheres or cellulose spheres (e.g., CELPHERE® CP-203) using a fluid-bed coater equipped with a bottom-spray Wurster insert. These corticosteroid-coated beads can then be taste-masked by fluid-bed coating or by solvent coacervation as described herein.

In another embodiment, the compositions of the present invention can comprise corticosteroid particles (e.g., crystals), coated with a taste-masking layer. The taste-masking layer (as described herein) can be applied to the corticosteroid particles by any suitable method, for example coacervation or fluidized bed coating methods. Alternatively, the compositions of the present invention can comprise a corticosteroid complexed with a cyclodextrin.

In one embodiment, the method of preparing the compositions of the present invention includes a taste-masking step. The taste-masked corticosteroid-containing particles of the compositions of the present invention (e.g., corticosteroid crystals, corticosteroid-containing microgranules or drug-layered beads) of the present invention can be prepared by various methods, including solvent coacervation with a water-insoluble polymer such as ethylcellulose. The water-insoluble polymer (e.g., ethylcellulose), a phase-inducer (e.g., polyethylene), and corticosteroid are loaded into a coacervation tank containing cyclohexane. The mixture in the tank is heated to about 80° C. to dissolve the ethylcellulose, and then slowly cooled under controlled conditions thereby causing phase-induced microencapsulation of corticosteroid particles by the ethylcellulose. Microencapsulation or coacervation refers to the process of applying a membrane by phase separation for imparting taste-masking (or sustained release) properties. Upon reaching ambient temperature, the suspension of microencapsulated corticosteroid particles are filtered, washed with fresh cyclohexane and dried to reduce residual solvent levels within acceptable limits (e.g., <4,000 ppm), in one embodiment less than 1,000 ppm. The coating weight of the microencapsulated corticosteroid particles can range from about 5% to about 30% including about 10%, 15%, 20%, and 25%, inclusive of all ranges and subranges therebetween. Examples of such a coacervation process are disclosed in U.S. Pat. Nos. 5,252,337, 5,639,475, 6,139,865 and 6,495,160.

Alternatively, the coacervation solution can comprise a mixture of the water-insoluble polymer (e.g., ethylcellulose) and a water-insoluble or gastrosoluble pore-former (e.g., calcium carbonate). The ratio of water-insoluble polymer to pore-former can range from about 50/50 to 95/05, including about 55/45, about 60/40, about 65/35, about 70/30, about 75/25, about 80/20, about 85/15, and about 90/10, including all ranges and subranges therebetween. The coating weight of the microencapsulated corticosteroid particles can range from about 5% to about 30% including about 10%, 15%, 20%, and 25%, inclusive of all ranges and subranges therebetween. In one embodiment, the coacervation step comprises suspending the drug-containing particles in a solution of water-insoluble ethylcellulose at 80° C. in the coacervation tank. During the cooling cycle, the micronized pore-former is introduced into the tank at a temperature of about 58° C., while constantly stirring the suspension to uniformly distribute the pore-former in the microcapsule-membrane, at the forming/hardening phase. Examples of such a coacervation process are disclosed in U.S. Patent Publication No. US 2006/0105038.

In one embodiment, the solid pharmaceutical composition of the present invention is in the form of an orally disintegrating tablet (ODT). In one such embodiment the ODT comprises drug particles and rapidly dispersing granules, wherein the drug particles comprise the corticosteroid, and the rapidly dispersing granules comprise a disintegrant and a sugar alcohol and/or saccharide. The drug particles may comprise, for example, corticosteroid crystals with or without a coating, corticosteroid-layered beads or granulates of corticosteroid with one more additional components. In certain embodiments the ODT is in the form of a wafer or film (for example those described in U.S. Pat. Nos. 6,534,549, 7,125,564, etc.).

In one embodiment of the present invention the solid composition comprises a lyophilized matrix, wherein the lyophilized matrix comprises corticosteroid and an excipient. Suitable excipients include mannitol, xylitol, sorbitol, maltol, maltitol, lactose, sucrose, maltose, and combinations thereof.

The amount of corticosteroid-containing granules in the solid compositions of the present invention can range from about 5% to about 50%, including about 5%, about 10%, about 15%, about 20%, about 25%, about 30%, about 35%, about 40%, about 45%, and about 50%, inclusive of all values, ranges, and sub-ranges therebetween. In one embodiment, the composition of the present invention is an ODT comprising about 30% by weight of corticosteroid-containing granules.

One embodiment of a method for producing pleasant tasting corticosteroid ODT formulations of the present invention, comprising corticosteroid microparticles with a mean particle size of about 100-400 μm, comprises (i) preparing drug-containing cores having corticosteroid crystals with a desired mean particle size, e.g., as microgranules, corticosteroid particles (e.g., crystals), or as drug-layered beads, (ii) preparing granules comprising a disintegrant, a sugar alcohol and/or a saccharide, and (iii) compressing a blend comprising the corticosteroid microparticles and the disintegrant granules, optionally with pharmaceutically acceptable flavorant(s), sweetener(s), other disintegrant(s), colorant(s) and/or compression aides such as microcrystalline cellulose in sufficient quantities into the ODT form using a tablet press, such as a rotary tablet press equipped with an external lubrication system to lubricate the punches and dies prior to compression. These ODT tablets rapidly disintegrate upon exposure to the saliva in the mouth into a smooth, easy-to-swallow suspension with no gritty aftertaste.

In another embodiment, the method for preparing ODT formulations of the present invention comprising corticosteroid microparticles with a mean particle size of about 100-400 μm can also include a unit process for taste-masking the corticosteroid-containing particles (e.g., corticosteroid crystals, corticosteroid-containing granules or drug-layered beads) by coacervation or fluid bed coating prior to blending and compression into ODT tablets. For example, corticosteroid crystalline material with an average particle size range of about 1-200 more particularly about 50-150 μm can be coated with a taste-masking layer by either fluid-bed coating or solvent coacervation in accordance with other aspects of the invention. Corticosteroid crystalline material with a mean particle size of about 5-50 μm can also be taste-masked by solvent coacervation as described herein.

In another embodiment, the compositions of the present invention can be orally disintegrating tablets prepared by mixing corticosteroid microgranules or taste-masked corticosteroid microparticles, one or more flavoring agents, a sweetener, rapidly-dispersing microgranules, microcrystalline cellulose, and an additional disintegrant, and compressing this mixture into orally disintegrating tablets. The orally disintegrating tablets formed thereby rapidly disintegrate on contact with saliva in the buccal cavity, and have a pleasant taste (good creamy mouth feel) and provide rapid, substantially-complete release of the dose in the stomach.

In yet another embodiment, the compositions of the present invention may be orally disintegrating tablets formed by compressing a composition comprising corticosteroid-containing particles, rapidly-dispersing granules, and optionally flavoring agents, sweeteners, and other pharmaceutically acceptable excipients in a tablet press equipped with an externally lubricating system to pre-lubricate dies and punches, thereby providing a tablet formulation otherwise free of lubricant. The orally disintegrating tablets thus produced typically exhibit sufficient hardness and sufficiently low friability to be suitable for packaging in HDPE bottles and push-through film backed or peel-off paper backed blister packs using conventional equipment for storage, transportation and commercial distribution.

In another embodiment, a method of manufacturing orally disintegrating tablets of the present invention comprises the following steps: (a) preparing corticosteroid-containing microgranules by granulating crystalline corticosteroid material having an average particle size of about 5-50 μm and one or more diluents/fillers such as lactose, mannitol, microcrystalline cellulose and mixtures thereof, with a polymeric binder in a high-shear granulator or a fluid-bed coater; (b) granulating one or more sugar alcohols and/or saccharides, each having an average particle diameter of not more than about 30 with a disintegrant such as crospovidone, using water or an alcohol-water mixture in a conventional granulator, and drying the granulate in fluid-bed equipment or a conventional oven to produce rapidly-dispersing microgranules with an average particle size of not more than about 400 μm, as described in U.S. Patent Publication No. US 20050232988; filed Apr. 19, 2004; (c) blending the corticosteroid microgranules of step (a) with one or more flavoring agents, a sweetener, microcrystalline cellulose, additional disintegrant, and the rapidly-dispersing microgranules of step (b); and (d) compressing the blend of step (c) into tablets using e.g. a conventional rotary tablet press equipped with an external lubrication system to pre-lubricate the dies and punches.

In another embodiment, a method of manufacturing orally disintegrating tablets of the present invention comprises the following steps: a) preparing a drug-containing core particle (e.g., corticosteroid crystals, drug-layered beads, or corticosteroid-containing microgranules) by granulating the drug and optionally one or more diluents/fillers such as lactose, mannitol, microcrystalline cellulose and mixtures thereof with a polymeric binder in a high-shear granulator or a fluid-bed coater, or drug-layering on an inert particle (60-100 mesh sugar sphere or cellulose sphere, e.g., CELPHERE® CP-203) from a solution/suspension comprising a polymeric binder and the drug in a fluid-bed coater and optionally applying a seal-coat (e.g., OPADRY® Clear); b) taste-masking core particles by microencapsulation, e.g. by solvent coacervation or fluid-bed coating with a water-insoluble polymer such as ethylcellulose, or with a mixture of a water-insoluble functional polymer and a water-soluble/gastrosoluble pore-former (e.g., ethylcellulose and sodium chloride or calcium carbonate at a ratio ranging from about 50/50 to 95/5) to produce pleasant-tasting microparticles with a desired particle size distribution (e.g., an average particle size of not more than about 400 μm, or an average particle size of not more than about 300 μm); c) granulating one or more sugar alcohols and/or saccharides, each of which has an average particle diameter of not more than about 30 μm, with a disintegrant such as crospovidone, as disclosed herein; d) blending the taste-masked microparticles of step (b) with one or more flavoring agents, a sweetener, microcrystalline cellulose, additional disintegrant, and rapidly-dispersing microgranules of step (c); and e) compressing the blend of step (d) into tablets using e.g. a conventional rotary tablet press equipped with an external lubrication system to pre-lubricate the dies and punches.

Example 1

Fluticasone Propionate Microgranules A: Mannitol 25 (91.2% w/w) and Crospovidone XL-10 (4.8% w/w) at a ratio of 95/5 are co-milled individually by passing the mixture through a COMIL® milling apparatus, equipped with 0.225" spacers, at a speed of about 1400-1500 rpm. The mannitol, crospovidone, and fluticasone propionate (4% w/w) crystalline material are blended for about 3-5 minutes to mix the ingredients. A Glatt GPCG-3 fluid-bed apparatus equipped with a top spray granulation chamber and a granulation bowl is charged with the pre-blend of mannitol, crospovidone, and fluticasone propionate (batch size: 1500 g) and granulated by spraying purified water (nozzle: 1.2 mm tip) at an atomization pressure of about 1.25 bar and at a spray rate of 30-50 mL/min and an outlet temperature of >70° C. and at a product temperature of >33° C. The wet mass is dried until the moisture level (the percent loss on drying) is less than about 1%.

Tableting: A Hata production tablet press equipped with a vacuum transfer system, tablet de-duster, a metal detector, and a Matsui Ex-lube system were set up according to standard operating procedures. Magnesium stearate was used as a processing aid, i.e., to externally lubricate the punch and die surfaces and was therefore present in only trace amounts on the tablets. The weight range for the tablets was typically ±5% of the target tablet weight. The Ex-lube system was started to ensure that the lubricant was spraying properly when the tablet press was running. The tableting parameters, such as fill depth (mm), pre-compression position (mm or kN) and main compression position (mm or kN) were adjusted on the press in order to produce 4 mg tablets that meet the exemplary specifications listed below:

TABLE

Tablet Parameters

| Parameter | Target | Range |
|---|---|---|
| Weight (mg) | 100 | 95-105 |
| Thickness (mm) | 2.4 | 2.0-2.8 |
| Hardness (N) | 28 | 8-48 |
| Friability | NMT 0.6% | 1.0% |
| Weight 10 tablets (g) | 1.0 g | 0.96-1.04 |

Following the successful set-up, the press was run in 'Automatic Mode' until completion. During the run, tablets were sampled periodically to ensure that the tablets produced would meet the specifications listed above.

The tablets are tested in the USP <701> Disintegration test and disintegrate in about 60 seconds or less.

Example 2

A liquid is prepared by mixing 89.8% of 95% ethanol, by weight 5% ethylcellulose, 0.2% by weight oleic acid and 5% fluticasone propionate. Upon dabbing on to a mucosal surface a film is formed which adheres readily to skin or mucosal tissues.

An ethyl alcohol based gel is prepared by mixing the following components: 67% by weight of 95% ethyl alcohol; 8% by weight ethylcellulose; 2% by weight hydroxypropylcellulose; 2% by weight polyacrylic acid; 14% by weight menthol; 5% by weight water USP; and 2% by weight fluticasone propionate. A smooth, slightly opaque and sticky gel is formed.

The film, resulting from the application of this gel to a mucosal surface adheres to the surface and requires mechanical effort for its removal.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. An orally disintegrating tablet comprising:
   (i) about 0.5 mg to about 6 mg of a corticosteroid selected from fluticasone propionate or budesonide; and
   (ii) at least one disintegrant;
   wherein upon administration a therapeutically effective amount of the corticosteroid is deposited topically in the esophagus,
   wherein the orally disintegrating tablet disintegrates within 60 seconds when tested using the USP <701> Disintegration Test, and
   wherein the orally disintegrating tablet has a hardness of 4-48 N or a friability of not more than 1%.

2. The orally disintegrating tablet of claim 1, comprising about 0.5 mg to about 2 mg of the corticosteroid.

3. The orally disintegrating tablet of claim 1, comprising about 3 mg of the corticosteroid.

4. The orally disintegrating tablet of claim 1, comprising a sugar alcohol and/or saccharide.

5. The orally disintegrating tablet of claim 1, wherein the orally disintegrating tablet comprises drug particles and rapidly dispersing granules, wherein the drug particles comprise the corticosteroid and at least one excipient, and the rapidly dispersing granules comprise the disintegrant and a sugar alcohol and/or saccharide.

6. The orally disintegrating tablet of claim 5, wherein the rapidly dispersing granules have an average particle size of less than about 300 µm, and each of the disintegrant and sugar alcohol and/or saccharide have an average particle size of about 1-30 µm.

7. The orally disintegrating tablet of claim 5, wherein the drug particles have an average particle size of about 100-400 µm.

8. The orally disintegrating tablet of claim 5, wherein the drug particles have an average particle size of about 100-400 µm, the rapidly dispersing granules have an average particle size of less than about 300 µm, and each of the disintegrant and sugar alcohol and/or saccharide have an average particle size of about 1-30 µm.

9. The orally disintegrating tablet of claim 2, wherein the corticosteroid is budesonide.

10. The orally disintegrating tablet of claim 5, wherein the orally disintegrating tablet comprises about 3 mg of fluticasone propionate.

11. The orally disintegrating tablet of claim 3, wherein the corticosteroid is fluticasone propionate.

12. The orally disintegrating tablet of claim 8, wherein the orally disintegrating tablet comprises about 3 mg of fluticasone propionate.

13. The orally disintegrating tablet of claim 1, wherein the disintegrant is crospovidone, sodium starch glycolate, cross-linked carboxymethyl cellulose, low-substituted hydroxylpropylcellulose, mannitol, xylitol, sorbitol, maltol, maltitol, lactose, sucrose, maltose, or combinations thereof.

14. The orally disintegrating tablet of claim 13, wherein the disintegrant is crospovidone.

15. The orally disintegrating tablet of claim 5, wherein the sugar alcohol and/or saccharide is mannitol, sorbitol, xylitol, maltitol, arabitol, ribitol, dulcitol, iditol, isomalt, lactitol, erythritol, lactose, sucrose, maltose, or combinations thereof.

16. The orally disintegrating tablet of claim 15, wherein the sugar alcohol is mannitol.

17. The orally disintegrating tablet of claim 5, wherein the ratio of disintegrant to sugar alcohol, saccharide or mixture thereof in the rapidly dispersing microgranules ranges from about 90/10 to about 99/01.

18. The orally disintegrating tablet of claim 1, wherein the orally disintegrating tablet disintegrates within 60 seconds when tested in simulated saliva fluid using the USP <701> Disintegration Test.

19. The orally disintegrating tablet of claim 1, wherein the orally disintegrating tablet disintegrates within 30 seconds when tested using the USP <701> Disintegration Test.

20. A method for treating eosinophilic esophagitis comprising administering to a patient in need thereof the orally disintegrating tablet according to claim 1.

21. The method of claim 20, wherein the orally disintegrating tablet comprises about 3 mg of fluticasone propionate.

22. The method of claim 20, wherein the orally disintegrating tablet comprises about 0.5 mg to about 2 mg of budesonide.

23. The orally disintegrating tablet of claim 1, wherein the orally disintegrating tablet has a hardness of 4-48 N.

24. The orally disintegrating tablet of claim 1, wherein the orally disintegrating tablet has a friability of not more than 1%.

25. The orally disintegrating tablet of claim 1, wherein the orally disintegrating has a hardness of 4-48 N and a friability of not more than 1%.

26. The orally disintegrating tablet of claim 1, wherein the orally disintegrating tablet has a friability of not more than 0.6%.

27. The orally disintegrating tablet of claim 25, wherein the orally disintegrating tablet has a friability of not more than 0.6%.

28. The orally disintegrating tablet of claim 27, wherein the orally disintegrating tablet has a thickness of 2-2.8 mm.

29. The orally disintegrating tablet of claim 14, wherein the orally disintegrating tablet comprises about 3 mg of fluticasone propionate.

30. The orally disintegrating tablet of claim 16, wherein the orally disintegrating tablet comprises about 3 mg of fluticasone propionate.

31. The method of claim 20, wherein the orally disintegrating tablet disintegrates within 60 seconds when tested in simulated saliva fluid using the USP <701> Disintegration Test.

32. The method of claim 20, wherein the orally disintegrating tablet disintegrates within 30 seconds when tested using the USP <701> Disintegration Test.

33. The orally disintegrating tablet of claim 28, wherein the orally disintegrating tablet comprises about 3 mg of fluticasone propionate.

34. The orally disintegrating tablet of claim 28, wherein the orally disintegrating tablet comprises about 0.5 mg to about 2 mg of budesonide.

* * * * *